US010563998B1

(12) United States Patent
Rivera

(10) Patent No.: US 10,563,998 B1
(45) Date of Patent: Feb. 18, 2020

(54) COMMUNITY-BASED TRANSPORTATION SERVICES SYSTEM AND METHOD

(71) Applicant: Nelson T. Rivera, Seaside, CA (US)

(72) Inventor: Nelson T. Rivera, Seaside, CA (US)

( * ) Notice: Subject to any disclaimer, the term of this patent is extended or adjusted under 35 U.S.C. 154(b) by 0 days.

(21) Appl. No.: 15/666,464

(22) Filed: Aug. 1, 2017

Related U.S. Application Data

(60) Provisional application No. 62/370,364, filed on Aug. 3, 2016.

(51) Int. Cl.
| | |
|---|---|
| *G01C 21/36* | (2006.01) |
| *G01C 21/34* | (2006.01) |
| *G08G 1/14* | (2006.01) |
| *G01S 19/42* | (2010.01) |
| *A61B 5/00* | (2006.01) |

(52) U.S. Cl.
CPC ........ *G01C 21/3614* (2013.01); *A61B 5/4845* (2013.01); *G01C 21/3476* (2013.01); *G01C 21/3661* (2013.01); *G01C 21/3667* (2013.01); *G01C 21/3682* (2013.01); *G01C 21/3685* (2013.01); *G01C 21/3697* (2013.01); *G01S 19/42* (2013.01); *G08G 1/144* (2013.01); *G08G 1/148* (2013.01)

(58) Field of Classification Search
CPC .............. A61B 5/4845; G01C 21/3476; G01C 21/3661; G01C 21/3667; G01C 21/3682; G01C 21/3685; G01C 21/3697; G01S 19/42; G08G 1/144; G08G 1/148
USPC ........................................................ 701/426
See application file for complete search history.

(56) References Cited

U.S. PATENT DOCUMENTS

| | | | |
|---|---|---|---|
| 4,093,945 | A | 6/1978 | Collier et al. |
| 6,026,674 | A | 2/2000 | Gammenthaler |
| 6,650,250 | B2 | 11/2003 | Muraki |
| 7,912,627 | B2 | 3/2011 | Downs et al. |
| 8,779,940 | B2 | 7/2014 | Amir |
| 8,779,941 | B2 | 7/2014 | Amir |
| 8,890,715 | B2 | 11/2014 | Geelen |
| 8,994,560 | B2 | 3/2015 | Anderson et al. |
| 9,073,431 | B2 | 7/2015 | Takahashi |

(Continued)

FOREIGN PATENT DOCUMENTS

EP 2832577 A2 2/2015

*Primary Examiner* — Maceeh Anwari
(74) *Attorney, Agent, or Firm* — Nelson T. Rivera

(57) ABSTRACT

A community-based transportation services system. The system includes a community-based transportation network that is comprised of a primary communication device, a cloud server and a parking inventory database. The system also includes at least one communication device communicatively coupled to said network for establishing a parking-spot communication link for allowing a first user to determine the location of available parking-spots for rent. The at least one communication device is also configured to establish a parking-registration link to allow a second user to register and offer at least one parking spot for rent. The system further includes a biosensor collector system communicatively coupled to said network and/or directly to the at least one communication device for establishing a sobriety-monitoring communication link. The data generated by the biosensor collector system allows a first user and a transportation provider to view and monitor the sobriety results of a transportation driver.

20 Claims, 21 Drawing Sheets

(56) References Cited

U.S. PATENT DOCUMENTS

| | | |
|---|---|---|
| 9,123,034 B2 | 9/2015 | Rydbeck et al. |
| 9,228,997 B2 | 1/2016 | Keays |
| 9,239,323 B2 | 1/2016 | Keays |
| 9,299,256 B2 | 3/2016 | Chen et al. |
| 9,417,232 B2 | 8/2016 | Keays et al. |
| 9,418,550 B2 | 8/2016 | Geelen |
| 9,443,428 B2 | 9/2016 | Amir |
| 9,589,466 B2 | 3/2017 | Huang |
| 9,666,074 B2 | 5/2017 | Nicoll et al. |
| 9,704,401 B2 | 7/2017 | Akavaram et al. |
| 2002/0127623 A1 | 9/2002 | Minshull et al. |
| 2003/0162536 A1 | 8/2003 | Panico |
| 2005/0241871 A1 | 11/2005 | Kuhlman et al. |
| 2006/0170566 A1 | 8/2006 | Slemmer et al. |
| 2006/0250278 A1 | 11/2006 | Tillotson et al. |
| 2006/0253711 A1* | 11/2006 | Kallmann ............ B60K 28/063 713/186 |
| 2007/0040701 A1 | 2/2007 | Browne et al. |
| 2008/0048885 A1 | 2/2008 | Quinn |
| 2010/0017084 A1 | 1/2010 | Riegel |
| 2011/0022427 A1 | 1/2011 | Dayan |
| 2011/0099040 A1 | 4/2011 | Felt et al. |
| 2011/0106425 A1 | 5/2011 | Trum et al. |
| 2011/0106426 A1 | 5/2011 | Tertoolen |
| 2011/0109480 A1 | 5/2011 | Huijnen |
| 2011/0133957 A1 | 6/2011 | Harbach et al. |
| 2011/0140922 A1 | 6/2011 | Levy et al. |
| 2012/0056758 A1 | 3/2012 | Kuhlman |
| 2012/0075094 A1 | 3/2012 | Keays |
| 2012/0098677 A1 | 4/2012 | Geelen |
| 2012/0136997 A1 | 5/2012 | Yan et al. |
| 2012/0161984 A1 | 6/2012 | Amir |
| 2012/0161985 A1 | 6/2012 | Amir |
| 2012/0161986 A1 | 6/2012 | Amir |
| 2012/0200430 A1 | 8/2012 | Spahl |
| 2012/0262305 A1 | 10/2012 | Woodard et al. |
| 2012/0265434 A1 | 10/2012 | Woodard et al. |
| 2013/0021153 A1 | 1/2013 | Keays |
| 2013/0057686 A1 | 3/2013 | Genc et al. |
| 2013/0176147 A1 | 7/2013 | Anderson et al. |
| 2015/0084774 A1* | 3/2015 | Wojcik ............... A61B 5/082 340/573.1 |
| 2015/0130642 A1 | 5/2015 | Huang |
| 2015/0219620 A1 | 8/2015 | Hol et al. |
| 2015/0279213 A1 | 10/2015 | Balter et al. |
| 2016/0055749 A1 | 2/2016 | Nicoll et al. |
| 2016/0117925 A1 | 4/2016 | Akavaram et al. |
| 2016/0117926 A1* | 4/2016 | Akavaram ............ G08G 1/143 340/932.2 |
| 2016/0324478 A1 | 11/2016 | Goldstein |
| 2017/0132883 A1* | 5/2017 | Keays ................... G08B 1/08 |

* cited by examiner

COMMUNITY-BASED TRANSPORTATION SERVICES SYSTEM AND METHOD

PRIORITY CLAIM

This application claims priority to U.S. provisional application 62/370,364, entitled "Method and System for Managing and Locating Parking-Spots", filed on Aug. 3, 2016.

TECHNICAL FIELD

The present invention relates to transportation services, and more particularly, but not limited to, a community-based transportation services system and method configured to determine the location of parking-spots, register and offer parking-spots for rent or a fee, and monitor and determine the sobriety of a transportation driver.

BACKGROUND OF THE INVENTION

Massive urban development and an increase in the number of vehicles on road ways have reduced the availability of parking making it a scarce resource in many localities such as, but not limited to, cities, towns, metropolises, boroughs, neighborhoods villages or municipalities. This growing problem results in a huge imbalance between the supply of parking spaces readily available and the demand, particularly during peak travel times daily and/or seasonally.

In view of reduced availability of parking, drivers often end up stressing themselves out while searching for an available parking spot after using a navigation device and/or some type of navigation service to reach a destination point of interest especially for those drivers who are not familiar with a locality/area. In fact, drivers circling endlessly to find a vacant parking spot can be linked to many prominent problems generated in cities that negatively affect the quality of urban life which directly contributes to traffic congestion, pollution, increased driving hazards (both for other drivers and for pedestrians), and a reduction of public space.

To alleviate the arduous task of locating a parking-spot, some parking facilities advantageously provide visual indicators to show that there are parking spots readily available at their facilities. These facilities may include, but are not limited to, parking garages, parking lots and/or other types of parking facilities. However, these designated available parking-spot locations shown by beneficial visual indicators are typically not within the view of drivers who may be only a block away from the available parking facility or parking spot.

There are various application programs provided by businesses in the travel and/or transportation industry, technology industry, or service and luxury industry for communication devices that provide drivers or taxi and limousine services with directions to specific destination points of interest via application programs and/or navigational technologies. However, these communication devices do not include application programs that provide information about available parking-spots or facilities located within a preselect radius of a driver's destination point of interest or within the geographic earth location of the driver. These communication devices, including their application programs, are often not configured to locate available parking-spots during or prior to the driver traversing to a specific destination point of interest.

Enhancing the utilization and management of parking spaces available provides benefits and conveniences to both individuals such as, but not limited to, drivers and pedestrians and cities. Drivers would benefit from the implementation of a method and system for managing and reporting of available parking-spots because this would allow drivers to navigate through a locality/area more efficiently if they had access to a suitably configured application program on their mobiles devices for locating available parking-spots.

Another problem that consumers generally encounter with communication devices having application programs that provide transportation/taxi services is that these devices are not configured to allow the consumer to monitor and/or determine if it is safe or not to use the services of a taxi provider (e.g., UBER or LYFT or MOOVN app). Namely, consumers are not able to obtain beneficial information in real time to determine if a potential transportation/taxi driver is under the influence of controlled substances/drugs and/or alcohol. Similarly, transportation/taxi service providers currently do not have a means of monitoring the sobriety of its drivers while they are out in the field providing rides (i.e., taxi services) to consumers.

In light of the shortcomings in the prior art, there is clearly a need for the development and implementation of a method and system that allows drivers locate available parking-spots during or prior to the driver traversing to a destination point of interest, and there is also a clear need for a method and system that allows consumers and/or transportation providers to monitor and determine the sobriety of transportation/taxi drivers. Accordingly, the present invention fulfills these long-standing needs and desires in the art.

SUMMARY OF THE INVENTION

The present invention addresses issues related to the need of providing users/drivers engaged in the task of locating a parking spot and/or space with comprehensive information about the availability and location of parking spots and/or locations within a locality and/or area.

Another aspect of the invention is to provide a method and system that utilizes a system for determining the location of parking-spots or locations to reduce traffic congestion, pollution, driving hazards and to reduce the waste of public space related to unused parking spots.

An additional aspect of the invention includes at least one communication device, such as a mobile device, that will be configured to allow a first user to reserve an available parking-spot, request parking-spot availability and display an exact location of the available parking spots.

A further aspect of the invention is to provide a community-based method and system utilizing a network that connects subscribers (e.g., drivers and/or individuals/entities offering available parking spots to rent) and taxi service providers and/or entities.

The present invention is also suitably configured to allow users/subscribers (i.e., second user) to register parking spaces to the network which provides other users/subscribers/drivers (i.e., first user) with the opportunity to rent or pay a fee to use these parking spots/spaces.

In this disclosure, "user" refers to: a driver (i.e., first user) of a vehicle, and/or a mobile taxi app user, also referred to as a consumer and/or an individual/entity (i.e., second user) offering at least one parking spot to be stored in a parking inventory database for a driver to rent or pay a fee in order to advantageously park his or her vehicle in said parking spot, preferably for a predetermined length of time. "Vehicle" refers to, but is not limited to, a car, motorcycle, bicycle, airplane (hanger) or boat. "Subscriber or subscribers" refers to "a first user or the first user" (i.e., driver of a vehicle) and/or also refers to "a second user or the second user" (i.e., an individual or entity offering at least one parking spot for rent).

One aspect of the present invention includes a parking-register device and a user's communication device configured to update the availability of parking-spot inventory stored in the memory and/or database of a community-based transportation services network. The updating of available parking-spots can also be achieved by a single communication device.

The present invention will be further configured to advantageously generate a parking inventory database based on users/subscribers (i.e., second users) registering their parking spaces to the network, thereby allowing other users/subscribers (i.e., first user) to gainfully rent or pay a fee to use these parking spots/spaces that are stored in the inventory database. The inventory database is communicatively coupled to the community-based transportation services network.

One feature of the present invention is to provide a suitably configured community-based transportation services network that is highly adaptive in that it is able to communicate with at least one communication device to determine the location of parking-spots in a locality.

Another feature of the present invention includes a mobile device having an application program suitably adapted to locate parking-spots during or prior to a driver traversing to a specific destination point of interest in a specific jurisdiction/city/locality/area.

The application program utilized by at least one communication device of the present invention will be configured to locate parking spots within a preselected radius of the geographic earth location of a first user or of the destination point of interest selected by the first user.

The application program utilized by at least one communication device of the present invention is also configured to allow a first user (also subscriber) to select one or more parking-spots when attempting to park a vehicle in a jurisdiction/locality/area. In this disclosure, jurisdiction/locality refers to, but is not limited to, cities, towns, neighborhoods, counties, regions, boroughs, districts, provinces, communities, villages, metropolises, or municipalities.

The application program utilized by at least one communication device of the present invention is also configured to allow a first user (also subscriber) to monitor the availability of parking-spots within a pre-selected radius of a major event which advantageously allows the first user to find a parking-spot in a specific area that is not congested or saturated by event traffic. This feature can also help to control the amount of event traffic generated by users who choose to park away from the venue that is hosting the event which can help to avoid traffic jams.

The application program utilized by the mobile device for the present invention will be further configured to advantageously provide directions to the first user corresponding to the location, facility or parking-spot selected by the first user.

In this disclosure, "parking-spot" refers to, but is not limited to, parking facility, street parking, parking inventory, parking location, open spot, remote infrastructure, parking space, parking garage, parking lot, available parking, garage parking, private parking, carport parking, parking room, parking bay, parking place, hanger (airplane or vehicle parking) or parking area.

It is an additional feature of the present invention to provide at least one communication device that is communicatively coupled to a community-based transportation services network for establishing a parking-registration link. Also, at least one communication device, such as a parking-register device, will allow a second user (also subscriber) to register at least one parking spot with the community-based transportation services network to advantageously allow a first user to rent or pay a fee to park his or her vehicle in the at least one parking-spot.

One embodiment of the present invention provides a method and system that utilizes at least one communication device, such as a transportation-services device, having a software application program configured to allow a first user to select at least one parking-spot when attempting to park a vehicle and/or allow a second user to register at least one parking spot with the community-based transportation services network to allow a first user to rent or pay a fee to park his or her vehicle in the at least one parking-spot. In this disclosure, a transportation-services device is configured to advantageously carry out all the functions/steps/operation of both a user's communication device and a parking-register device in a single device.

A further aspect of the invention is to provide a method and system that identifies and determines the sobriety of transportation drivers via a software application program downloaded on a communication device such as a transportation-provider's communication device. This method and system allows consumers to determine if it is safe or not to use the services of a taxi provider since they will now be able to obtain beneficial information in real time from a network or directly from their communication device by using a biosensor collector device communicatively coupled to their device for determining the sobriety of potential taxi drivers.

In another embodiment, a method and system via a software application program downloaded on a biosensor collector system provides transportation/taxi providers with the ability to monitor and determine the sobriety of its drivers utilizing a biosensor collector device while said drivers are out in the field offering rides (i.e., taxi service) to consumers.

Consequently, for a better understanding of the present invention, its functional advantages and the specific objects attained by its uses, reference should be made to the accompanying drawings, claims and descriptive matter in which there are illustrated preferred embodiments of the invention.

DETAILED DESCRIPTION OF THE INVENTION

Introduction

Figure 1A:
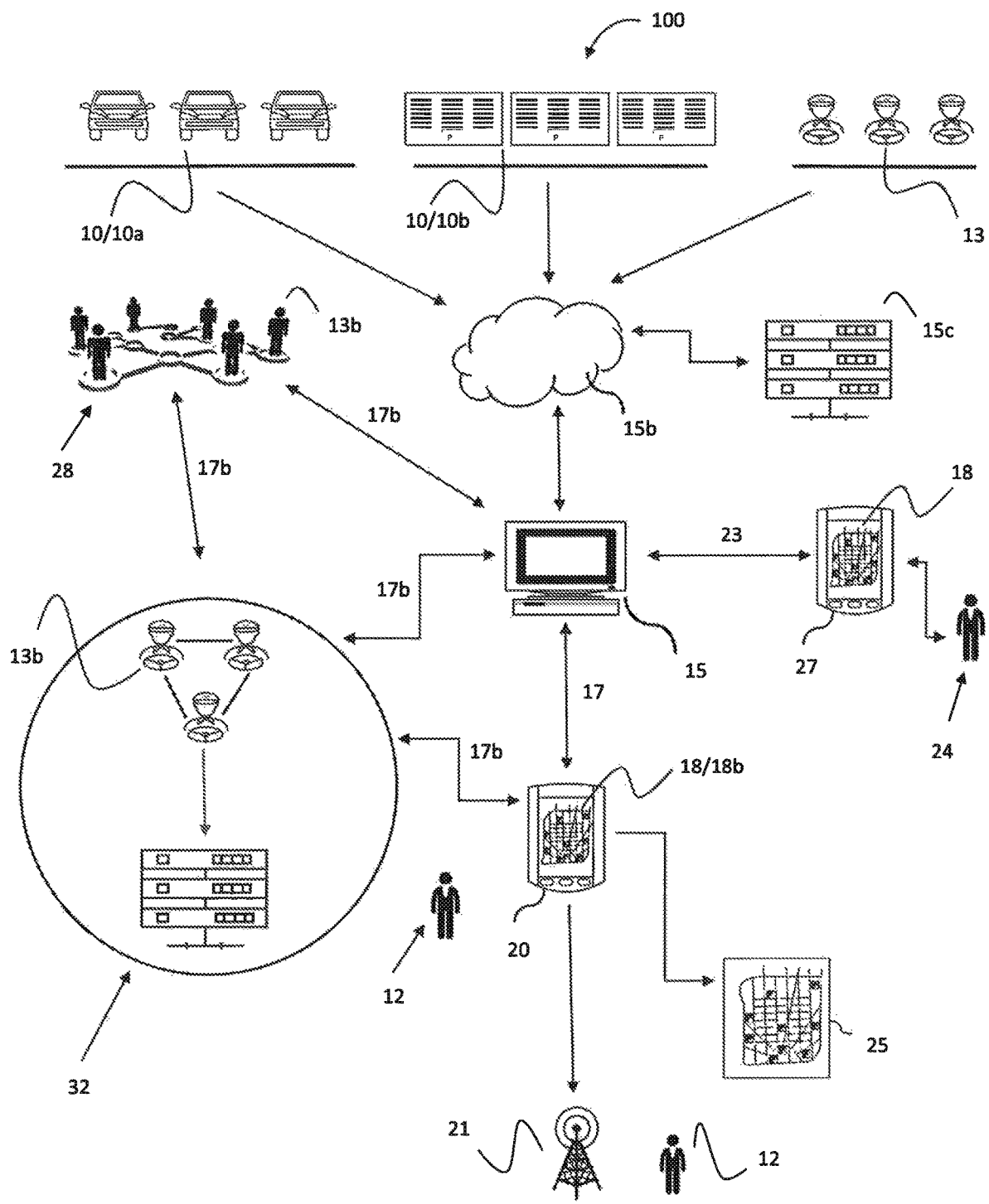
FIG. 1A shows the components of the community-based transportation services system.

The following detailed description is of the best currently contemplated modes of carrying out various embodiments of the invention. The description is not to be taken in a limiting sense, but is made for at least the purpose of illustrating the general principles of the invention, since the scope of the invention is best defined by the appended claims.

In one embodiment of the present invention, a method is provided for managing and determining the location of parking-spots stored in a database. The method being performed by one or more processors and comprising the steps of establishing a parking-spot communication link between a user's communication device and a community-based transportation services system; receiving information in real-time or non-real-time corresponding to a geographic earth location of a first user or of a destination point of interest selected by the first user; displaying the location of parking-spots stored in the parking inventory database to the first user, the parking-spots are located within a preselected radius/distance of the geographic earth location of the first user or of the destination point of interest selected by the first user; selecting a parking-spot stored in the database to allow the first user to park his or her vehicle; synchronizing the geographic earth location of the first user or of the selected destination point of interest to the location of the parking-spot selected by the first user; and providing directions to the first user corresponding to the parking-spot selected by the first user.

In another embodiment, a community-based transportation services system includes a user's communication device communicatively coupled to a community-based transportation services network; the community-based transportation services network having a processor; a memory communicatively coupled to the processor, the memory comprising instructions that when executed by the processor performs operations comprising: establishing a parking-spot communication link for allowing parking-spot data to be transmitted between the user's communication device and the community-based transportation services network; determining a geographic earth location of a first user or of a destination point of interest selected by the first user; displaying the location of parking-spots stored in the community-based transportation services network to the first user, the parking-spots being located within a preselected radius of the geographic earth location of the first user or of the destination point of interest selected by the first user; allowing the first user to select at least one parking-spot stored in the community-based transportation services network, thereby allowing the first user to rent or pay a fee to park his or her vehicle in the at least one parking-spot; synchronizing the geographic earth location of the first user or of the selected destination point of interest to the geographic earth location of the parking-spot selected by the first user; and providing directions to the first user corresponding to the parking spot selected by the first user for allowing the first user to park his or her vehicle.

Alternatively, a system is provided that is suitably configured to manage and determine the location of parking-spots stored in a database. The system advantageously includes at least one communication device communicatively coupled to a community-based transportation services network for establishing a parking-spot communication link; the parking-spot communication link is configured to receive information in real-time or non-real-time from a communication device; and the at least one communication device has a software application program configured to execute the following beneficial functions: determine a geographic earth location of a first user or of a destination point of interest selected by the first user; display the location of parking-spots to the first user, the parking-spots being located within a preselected radius of the geographic earth location of the first user or of the destination point of interest selected by the first user; select a parking-spot for allowing the first user to park his or her vehicle; synchronize the geographic earth location of the first user or of the selected destination point of interest to the location of the parking-spot selected by the first user; and advantageously provide directions to the first user corresponding to the parking spot selected by the first user.

Optionally, the community-based transportation services system further includes a parking-register device or at least one communication device. The parking-register device is communicatively coupled to the community-based transportation services network for allowing parking-register data to be transmitted between the parking-register device and the community-based transportation services network. The memory of the community-based transportation services network comprises instructions that when executed by the processor performs the operation comprising the function/operations of establishing a parking-location registration link for allowing a second user to register at least one parking spot with the community-based transportation services network.

In a further embodiment, a system is provided that advantageously identifies and determines the sobriety of a potential transportation driver. The system is comprised of a user's communication device communicatively coupled to a biosensor collector device. The biosensor collector device is configured to receive a saliva sample or condensate sample from air exhaled by the transportation driver for comparison to a DNA profile of said driver, and the DNA profile is stored in a database. A DNA sensor is communicatively coupled to the biosensor collector device to analyze the driver's cell material contained in the saliva sample or the condensate sample to determine if the cell material matches the driver's DNA profile stored in the database. If the driver' cell material matches his or her DNA profile stored in the database, the biosensor collector device is suitably configured to determine in real-time the sobriety of the driver by utilizing an intoxication substance sensor. The intoxication substance sensor is communicatively coupled to the biosensor collector device to analyze the cell material for detecting in real time the presence of a plurality of respective distinct intoxicating substances and/or alcohol content in the biological system of the driver, thereby allowing transportation providers and/or consumers to advantageously monitor and/or determine the sobriety of transportation/taxi drivers.

Alternatively, a system is provided for monitoring the sobriety of a transportation driver. The system is comprised of a biosensor collector device communicatively coupled to a community-based transportation services network, the community-based transportation services network having a processor; a memory communicatively coupled to the processor, the memory comprising instructions that when executed by the processor performs operations comprising: receiving sobriety-monitoring data associated with cell material disposed in a saliva or condensate sample being directed through a DNA sensor from air exhaled by a transportation driver or being directed directly through an intoxication substance sensor, the DNA sensor being communicatively coupled to the biosensor collector device; comparing the sobriety-monitoring data to DNA profile data associated with the transportation driver to determine if said cell material matches the DNA profile of the transportation driver for verifying the identification of said driver, the DNA profile data being stored in the community-based transportation services network; allowing the intoxication substance sensor to receive the sobriety-monitoring data by directing the saliva or condensate sample through the intoxication substance sensor or allowing the intoxication substance sensor to receive the sobriety-monitoring data by directing the saliva or condensate sample through the intoxication substance sensor if said cell material in the saliva or condensate sample matches the DNA profile data of the transportation driver, the intoxication substance sensor being communicatively coupled to the biosensor collector device; and analyzing the sobriety-monitoring data by using the intoxication substance sensor to sense and determine the sobriety of the transportation driver by detecting and measuring the presence of alcohol and/or at least one intoxicating substance in the biological system of said driver.

DETAILED DESCRIPTION

It should be understood that the foregoing relates to various embodiments of the invention and that modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

3. Parking Location/Registration System and Method:

Referring now to the drawings, FIG. 1A refers to one embodiment of the present invention depicting the components of a community-based transportation services system 100 configured to manage and determine the location of parking spots 10a/10b for a first user 12. The system 100 includes a user's communication device 20 (or a transportation-services device 2027) communicatively coupled to a community-based transportation services network 15 for establishing a parking-spot communication link 17. The community-based transportation services network 15 is comprised of a primary communication device 15, a cloud server 15b (or an application server, real-time communication server, collaboration server or a virtual server) and a parking inventory database 15c as shown in FIG. 1C. The parking-spot communication link 17 (also referred to as first communication link) is configured to transmit and receive information in real-time or non-real-time from the user's communication device 20 and from the community-based transportation services network 15. The user's communication device 20 will have an application program 18 that is suitably arranged to allow the first user 12 to select one or more parking-spots 10a/10b so that said user 12 can park his or her vehicle 11. The user's communication 20 device also includes a processor 20p communicatively coupled to memory 20m as shown in FIG. 1E. The memory and processor is external or internal to the device 20.

Optionally, the user's communication device 20 will be configured to advantageously include GNSS 20a and internet 20b capabilities. Alternatively, the user's communication device 20 can be a mobile device having a software application program, including but not limited to, a tablet computer, a personal computer, a server, a smartphone or a handheld computer.

Referring to FIGS. 1A and 1C, the community-based transportation services network 15 includes a memory 15m communicatively coupled to the processor 15p of the network 15. The memory includes instructions that when executed by the processor performs operations comprising: establishing a parking-spot communication link 17 for allowing parking-spot data to be transmitted between the user's communication device 20 and the community-based transportation services network 15; determining a geographic earth location of a first user 12 or of a destination point of interest 21 selected by the first user 12; displaying 25 the location of parking-spots 10a/10b stored in the community-based transportation services network 15 to the first user 12, the parking-spots 10a/10b being located within a preselected radius/distance of the geographic earth location of the first user 12 or of the destination point of interest 21 selected by the first user 12; allowing the first user 12 to select at least one parking-spot 10a/10b stored in the community-based transportation services network 15, thereby allowing the first user 12 to rent or pay a fee to park his or her vehicle 11 in the at least one parking-spot 10a/10b; synchronizing the geographic earth location of the first user 12 or of the selected destination point of interest 21 to the geographic earth location of the parking-spot 10a/10b selected by the first user 12; and providing directions to the first user 12 corresponding to the parking spot 10a/10b selected by the first user 12 for allowing said user 12 to park his or her vehicle 11.

In a further embodiment of the present invention, the system 100 is suitably adapted for subscribers 24 of the application program 18 (i.e., an owner 24 of at least one parking space 10b) to register and store at least one parking space 10a/10b to the community-based transportation services network 15 using a parking-register device 27 (or the transportation-services device 2027) (See also FIGS. 1A, 1B, 1F and 1G). This feature offered by the application program 18 which is downloaded on the parking-register device 27 will give subscribers 24 the opportunity to offer at least one parking spots/spaces 10b for rent to other subscribers 12 (e.g., drivers of vehicles 11), preferably for a limited period of time. When an owner 24 of a house is not at home for a predetermined length of time, he or she can offer other subscribers 12 of the system 100 the opportunity to rent his or her parking space 10b during this period or even offer to rent said parking space 10b when they are at home.

In one embodiment, a subscriber 24 owns or has access to at least one parking space 10a which is rentable to other subscribers 12. In this disclosure, "subscriber or subscribers" refers to a first user who is looking for a parking space 10a/10b and/or to a second user registering and storing a parking spot 10b to the system 100. Also, "house" or "home" in this disclosure refers to a place or an abode that a user 24 resides at or where the user 24 has access to a parking spot associated with his or her house/home or place of residence.

Subscribers 12 of the system 100 may own or have access to at least one vehicle 11 which is adapted to be parked in at least one of the registered parking spaces 10a/10b. Subscribers 24 of the application program 18 can advantageously rent out "parking-spots" 10b (after at least one parking-spot registered to the system) that are referred to in this disclosure as, but are not limited to, a parking facility, street parking, parking locations, open spots, remote infrastructure, parking spaces, parking garages, parking lots, garage parking, private parking spots, carport parking, parking rooms, parking bays, hanger, parking places or a parking areas, which are all capable of being rented to other subscribers 12.

For a community-based transportation services system 100 using a cloud server model 15b, users 12/24 are provided access to application software and databases. Cloud 15b providers manage the infrastructure and platforms on which the applications run. End users 12/24 access the applications on the cloud server 15b through a web browser or mobile application. Cloud computing will rely on the sharing of resources to attain coherence over a network.

The managing, determining and monitoring of parking data (i.e., inventory 10a/10b or parking spots 10a/10b) arises from users 12/24 sharing information about available parking. For example, drivers 12 may communicate information relating to a parking spot which is commonly known as crowdsourcing. Also, subscribers 24 can comprehensively provide such information about inventory by registering parking spots 10b with the system 100 or by providing updates about these parking-spots to the system 100. A major advantage is provided to the public when using this system 100 since parking spots/inventory 10a/10b can be utilized at capacity. Other forms of parking data may be obtained by historical parking data or near-by garage data, or direct sensing of available parking directly by the parking facility (See FIG. 5). Such data may be tagged as informal or formal monitored parking data.

In use, the user's communication device 20 (or the transportation-services device 2027) can be configured to advantageously allow a user/driver 12 to select a destination point of interest 21 or a parking facility 10a/10b by inputting a selected address, a region of interest, intersection, location, tourist attraction, or selecting a location on a display. It should be understood that the methods for selecting a location are only exemplary and techniques other than those described may be used.

In another embodiment, options may be provided on a display screen 25 that provides the user 12 with notification updates 250. A first selection option may include an option to continue its route to the selected parking facility. A second selection option may include a reselection process where a plurality of parking facilities is provided to the user 12 as options from which the user 12 can favorably choose from.

In a further embodiment, a map is displayed 25 to the user 12 identifying end-to-end, turn-by-turn navigation directions as typically provided by a navigation unit. The navigation instructions may beneficially include a downloaded map identifying the directions, the turn-by-turn instructions, and/or audio announcements. Furthermore, the downloaded map directions/instructions can be advantageously used in a parking facility even if a GNSS device or the like loses its signal via a caching mechanism advantageously accessible from at least one communication device via application program 18.

Figure 1B:
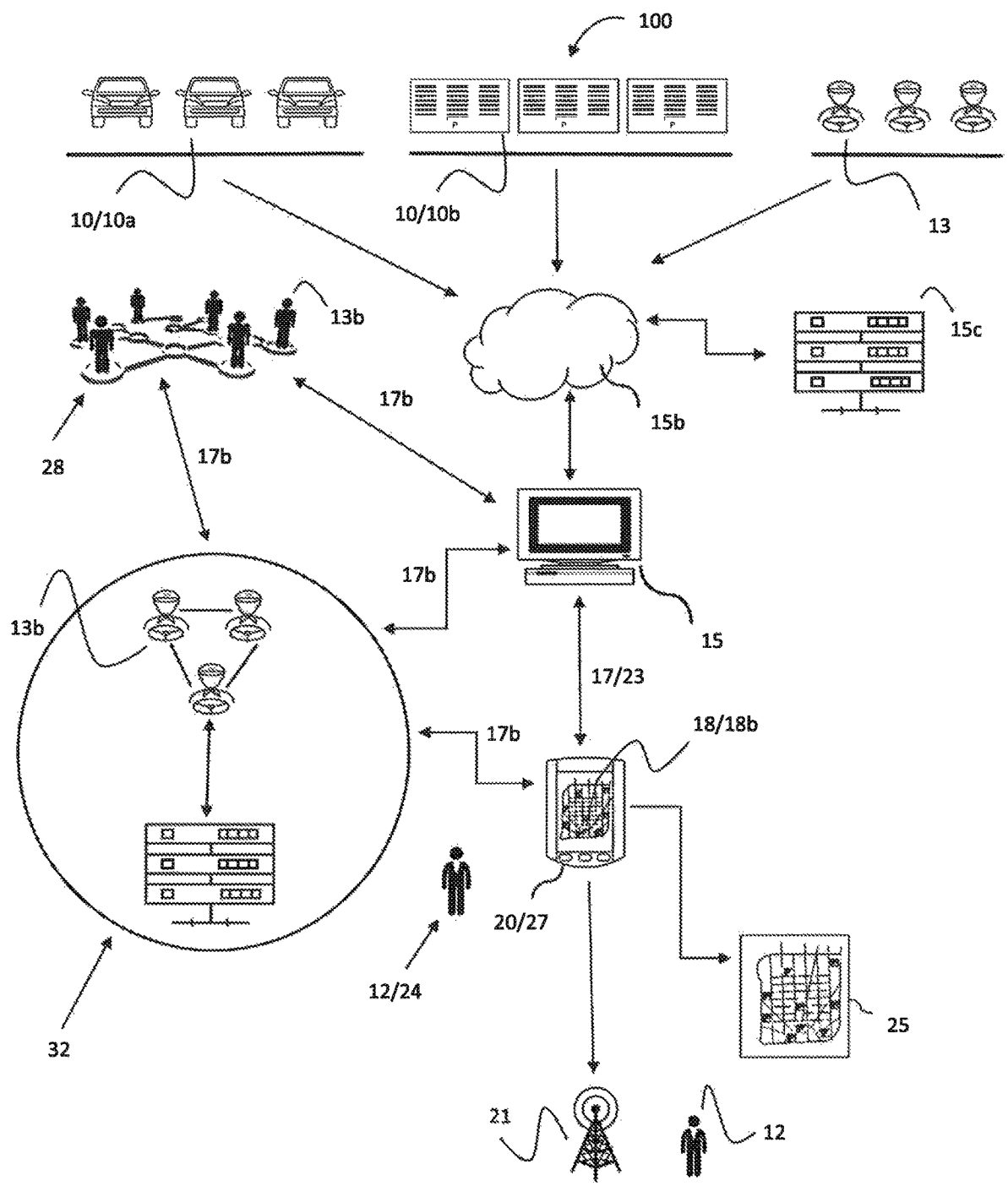
FIG. 1B is another embodiment of FIG. 1A showing that a user's communication device and parking-register device can be implemented on just a single device.
Figure 1C:
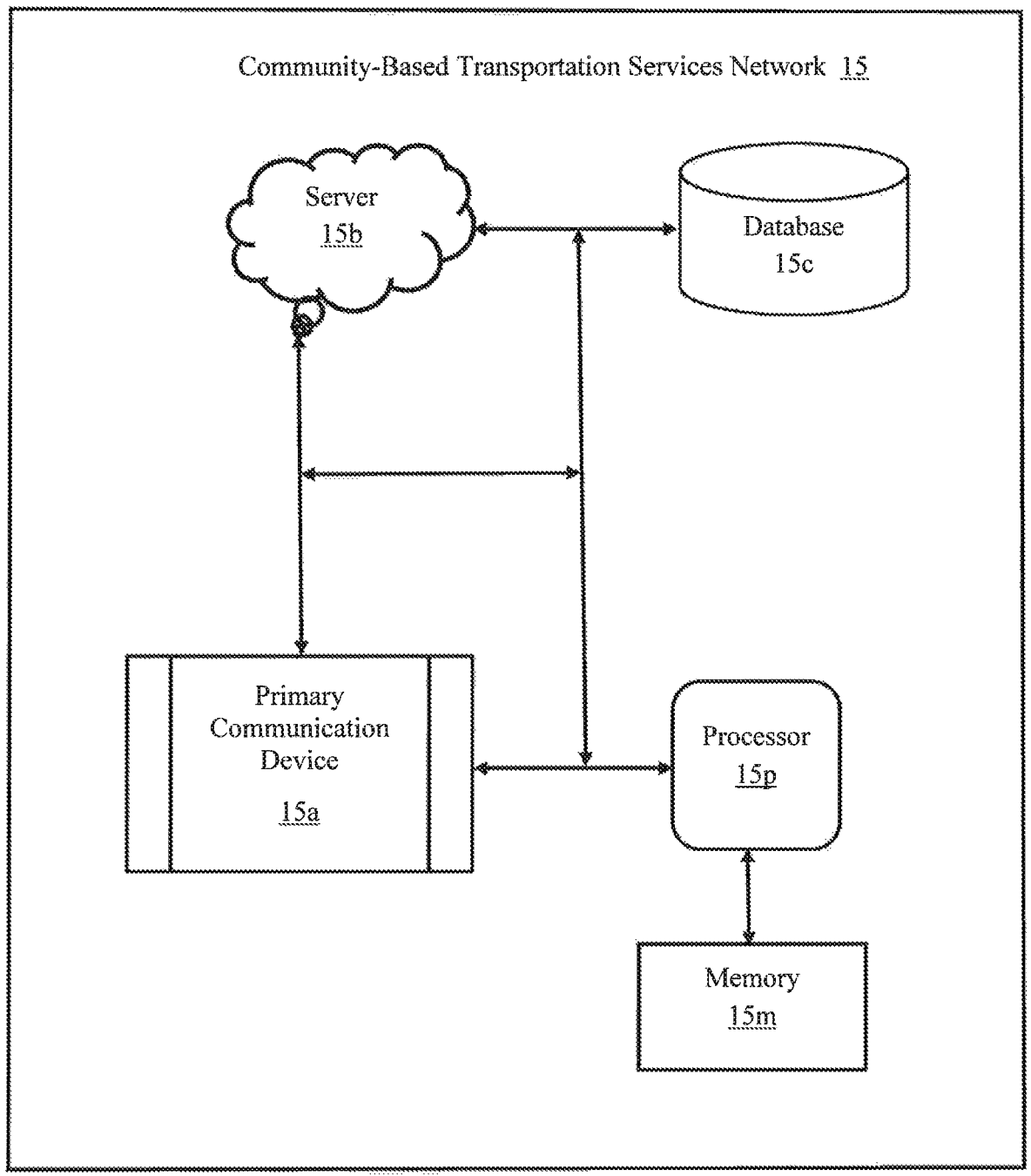
FIG. 1C shows the components of the community-based transportation services network.
Figure 5:
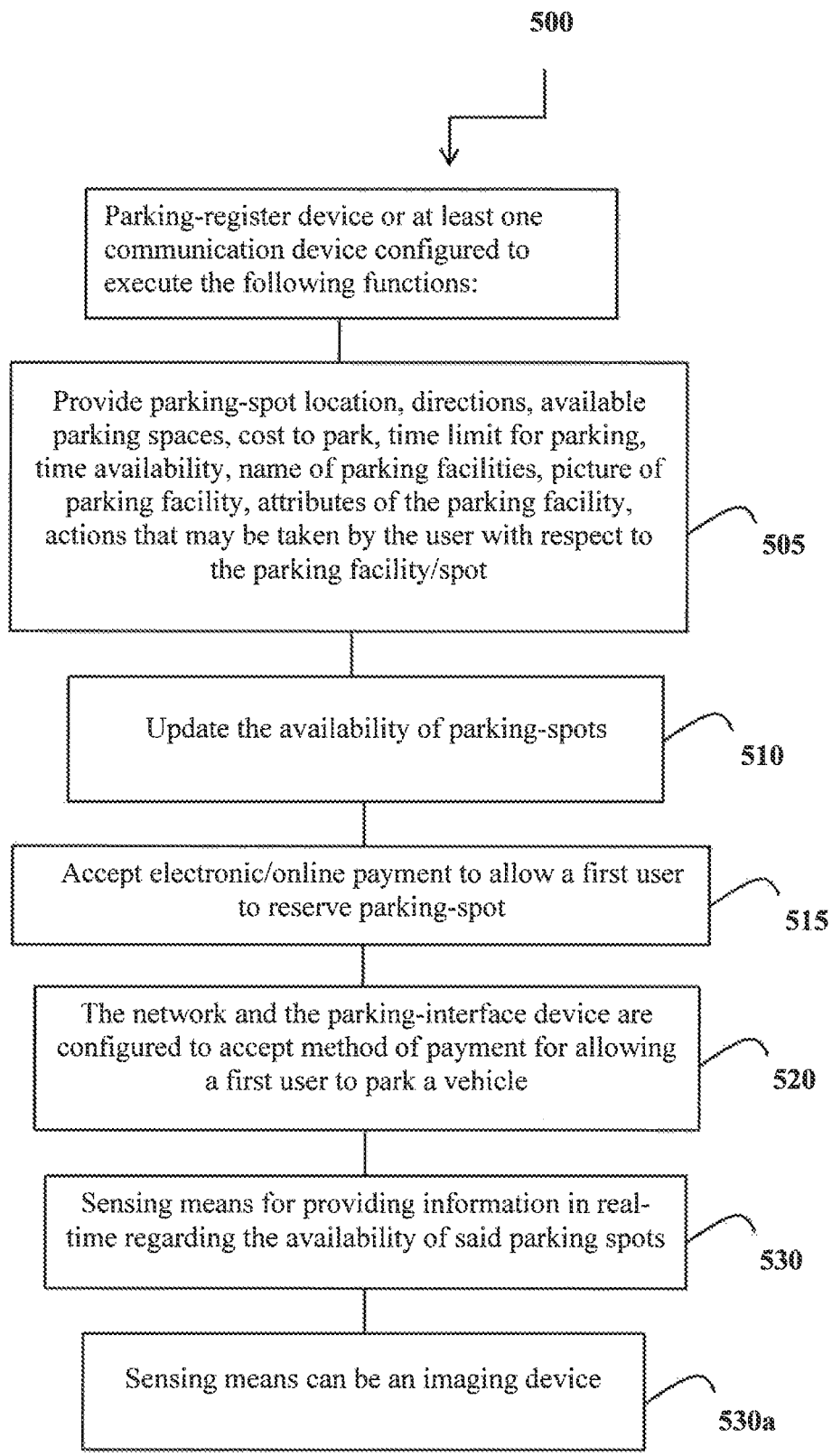
FIG. 5 represents a further process diagram showing the specific functions/operations that are executed by the parking-register device or transportation-services device for one embodiment of the present invention.

Optionally, each vehicle 11 may be equipped with various sensors and devices that generate signals that are communicated to the network 15 which is then stored and/or coupled to the network 15 by way of at least one communication device such as the user's communication device 20 or the parking-register device 27 for providing information relating to the position of the vehicle 11, positions of other vehicles, and parking lot information (See FIGS. 1A, 1B and 5). Moreover, other connected sensors and devices located remote from the vehicle 11 may also communicate parking related information to the network 15 (See FIG. 5). The information communicated to the network 15 may be stored in memory located in the database of the network 15 and processed as described herein to provide useful parking lot/space information for use by users/subscribers 12. The information stored in memory/database may be updated continually such that it is essentially real-time data.

The community-based transportation service system 100 includes a network 15 having a parking inventory database 15c of parking spaces available in a locality such as a city including their location, size, and level of demand. At least one communication device such as a user's mobile device 20 is provided that has an application program 18 for accessing the database 15c, the device 20 being configured to: select a vacant space, pay for a requested time period in a space, and update the database 15c for removing the space from the database 15c of available parking spots for the requested time duration. The device 20 also includes an augmented reality application program 18 to identify whether a parked vehicle 11 has paid for the space and to identify how much time remains via instructions stored in the memory and then executed by the processor of the network 15. The inventory of parking spaces 15 may accommodate an automobile or a plurality of smaller vehicles such as bicycles. Optionally, the mobile device 20 is programmed to extend the requested time duration for a particular parking spot. It is preferred that the database 15c be stored in the digital cloud 15b. It is also contemplated that the cost of the time duration requested will vary based on demand.

Optionally, the system 100 disclosed herein, incorporates an inventory of all existing parking spaces 10a/10b in a given locality/area such as cities including their location, size, and level of demand. The current system 100 also allows individual users 12 to navigate through an urban environment to efficiently find parking using an augmented reality application 18 on a mobile device. Once a space has been identified, individuals 12 can electronically validate their parking through an online payment system, and the payment, in turn, feeds back information to the system 100, removing the parking spot that has just been occupied from the database 15c of the network 15 of available parking spots for the time duration requested by the driver 12. Notably, the system 100 of the invention can free cities from physical installations of smart meters or sensors to identify available parking spots by using drivers 12 and subscribers 24 to collect and transmit this information thereof. The present invention also uses at least one communication device which may be a smart phone or a traditional cell phone.

Figure 1D:
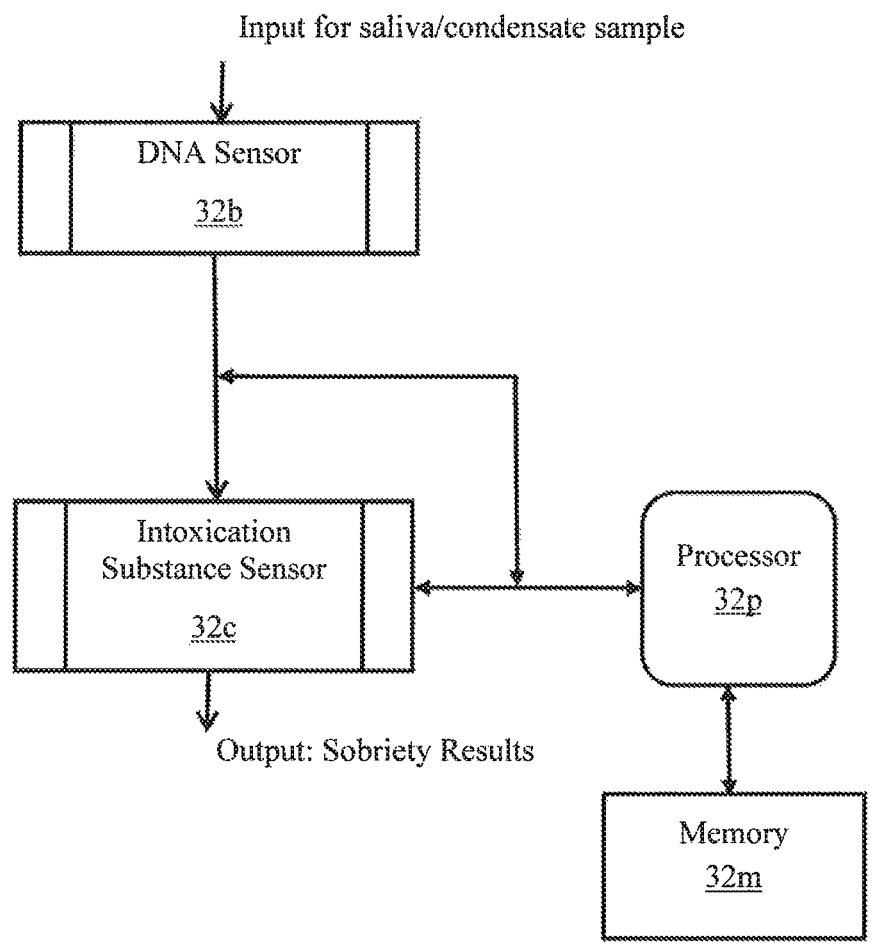
FIG. 1D is directed to the components of a biosensor collector device.
Figure 1E:
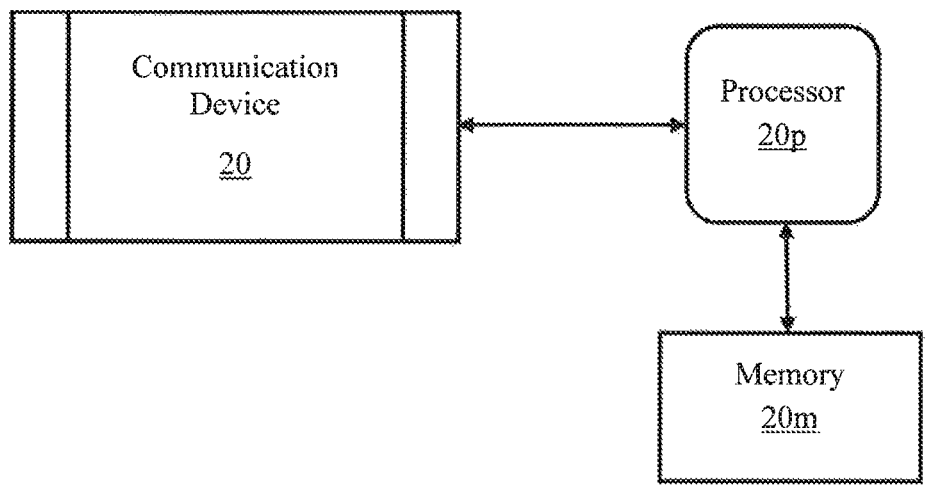
FIG. 1E is directed to the components of a user's communication device.
Figure 1F:
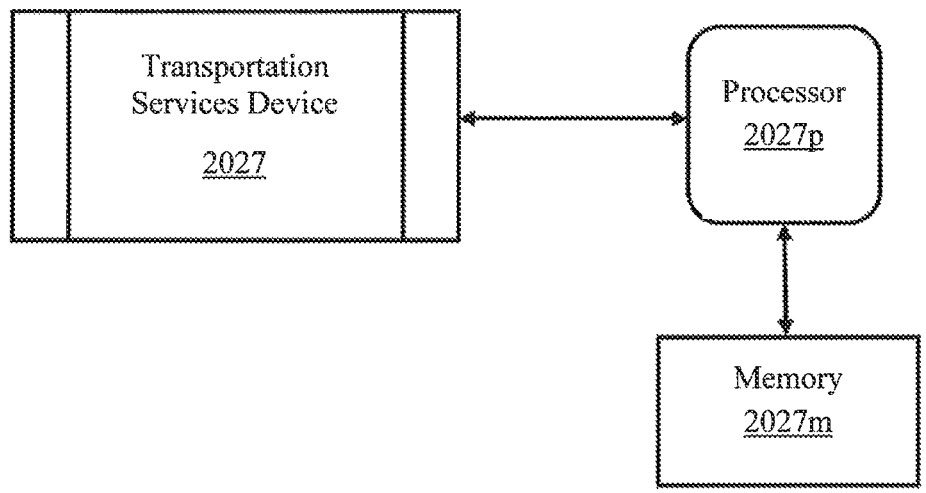
FIG. 1F is directed to the components of a transportation services device.
Figure 1G:
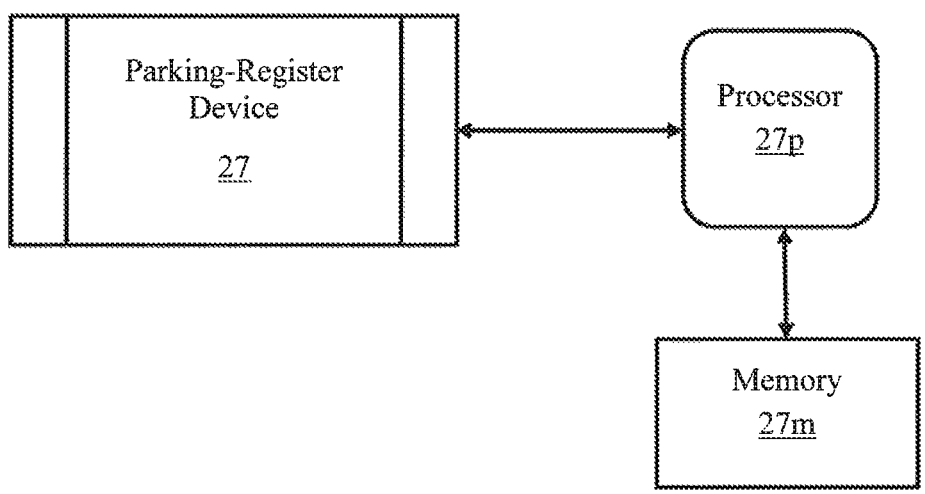
FIG. 1G is directed to the components of a parking-register device.
Figure 1H:
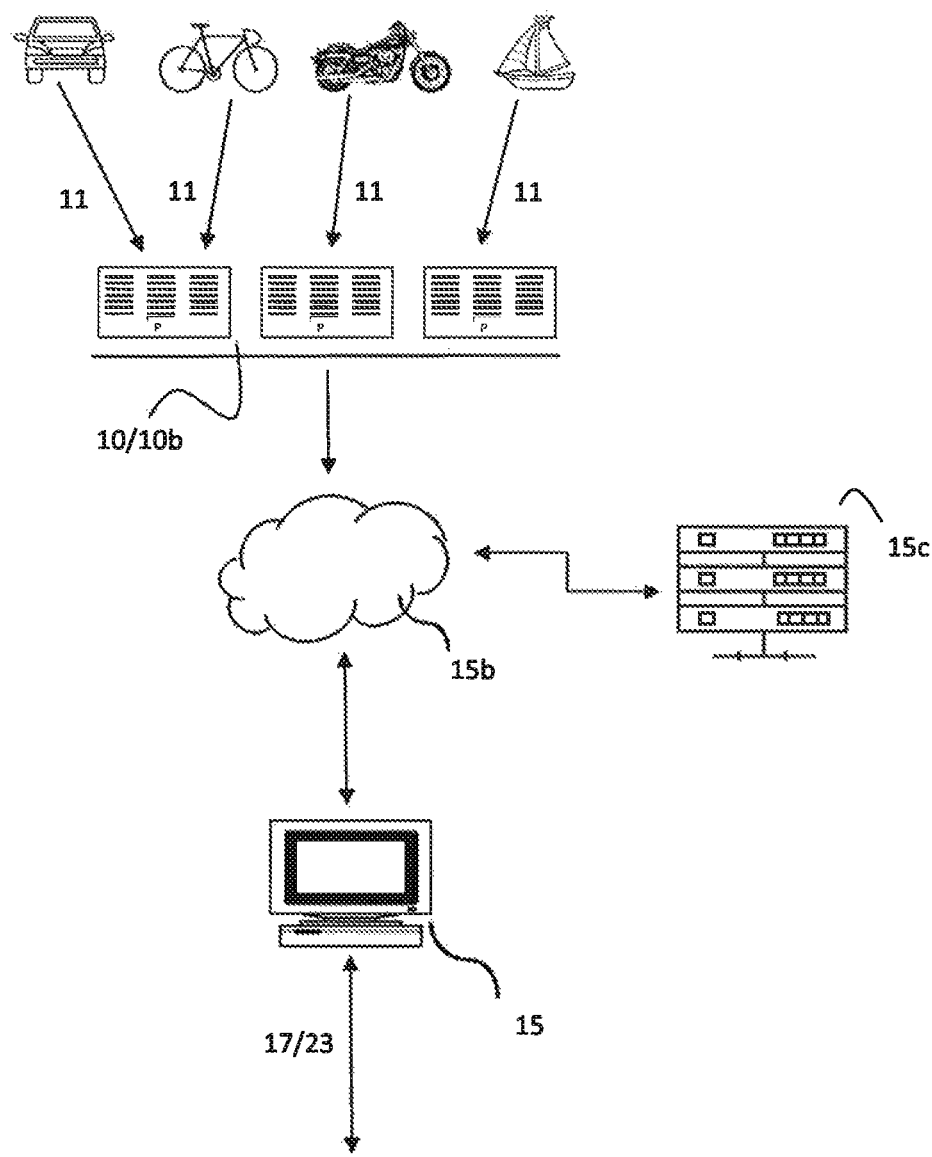
FIG. 1H is an expanded view of FIGS. 1A and 1B showing the types of vehicles 11 that can be registered, stored and parked 10b using the community-based transportation services network 100.

The system 100 of the invention is highly adaptive in that it can allocate a parking space 10a/10b for cars, boats, airplanes (hanger), motorcycles and bicycles, responding to the demands placed on the system 100 by its users 12 (See FIG. 1H). One parking space 10a/10b may be used either by a single car, motorcycle, a boat, a plurality of bicycles or an airplane (via a hanger). The invention not only encourages the use of bicycles but also formally deals with the occasional need to provide sufficient parking spaces for cyclists within cities. The system 100 of the invention also focuses on altering individuals' 12 behavior and developing parking enforcement to system users through civic engagement. If a driver 12 arrives at a parking spot that was supposed to be vacated by another driver 12, but has remained occupied, the driver has the option of reporting the violator using the mobile device's 20 (or the transportation-services device 2027) augmented reality system.

In a locality where parking is at a premium, the introduction of an infrastructure-less parking system 100 has the potential to reduce congestion on the roads and to help to improve air quality. Likewise, time spent searching for parking can be greatly reduced with an intelligent system 100 feeding back information in real time as to the location of available parking spaces. The system 100 of the invention can also be integrated into vehicle navigation systems that could further streamline the parking process.

In an alternative embodiment, the network 15 includes memory 15m communicatively coupled to a processor 15p. The processor 15p is configured to execute a predefined set of basic operations in response to receiving a corresponding basic instruction selected from a predefined native instruction set of codes. Further, the memory 15m comprises instructions that when executed by the processor performs operations/functions comprising: a first set of machine codes selected from the native instruction set configured to determine a geographic earth location of a first user 12 or of a destination point of interest 21 selected by the first user 12; a second set of machine codes selected from the native instruction set configured to display 25 the location of parking-spots 10a/10b stored in a parking inventory database 15c to the first user 12, the parking-spots 10a/10b being located within a preselected radius/distance of the geographic earth location of the first user 12 or of the destination point of interest 21 selected by the first user 12, wherein the parking inventory database 15c is communicatively coupled to the community-based transportation services network 15.

The memory 15m of the network further comprises instructions that when executed by the processor 15p performs operations/functions comprising: a third set of machine codes selected from the native instruction set configured to allow the first user 12 to select at least one parking-spot 10a/10b stored in the parking inventory database 15c; a fourth set of machine codes selected from the native instruction set configured to synchronize the geographic earth location of the first user 12 or of the selected destination point of interest 21 to the geographic earth location of the parking-spot 10a/10b selected by the first user 12; and a fifth set of machine codes selected from the native instruction set configured to provide directions to the first user 12 corresponding to the parking spot 10a/10b selected by the first user 12, wherein each of the first, second, third, fourth and fifth sets of machine code is stored in the memory.

In an optional embodiment, the memory 15m of the network further comprises instructions that when executed by the processor 15p performs operations/functions comprising: a sixth set of machine codes selected from the native instruction set configured to establish a parking-location registration link 23 for allowing a second user 24 to register at least one parking spot 10b with the community-based transportation services network 15, wherein the sixth set of machine code is stored in the memory.

Alternatively, the community-based transportation services network 15 includes at least one parking spot 10a/10b registered and stored in the parking inventory database 15c, for allowing the first user 12 to rent or pay a fee to park his or her vehicle 11 in the at least one parking-spot stored in the parking inventory database 15c.

In use, one of the first steps in utilizing the current system 100 and method 200 is to download the application program 18 to the communication device 20 and/or to the parking-register device 27 and/or the transportation-services device 2027 by creating an account and then logging into this account (See FIGS. 1A and 1B). The current system 100 and method 200 can also be incorporated to operate and/or function with other systems and methods offered by various taxi service providers 13b such as UBER, LYFT or MOOVN, including their platforms. To identify a parking spot close to a given position, a user 12 can either type the address of the place where he/she wants to park, select it on the touchscreen map, or use the GPS receiver (if the user's goal is to find a spot close to where he or she is standing or parked at that moment). The system 100 and method 200 at this stage will show available parking spots located within a preselected radius of the geographic earth location of the user 12 or of the destination point of interest 21 selected by the user 12. If the user 12 is looking for a parking place in some other area of town or locality, he or she can ask the system 100 to navigate him or her to available spots by giving his or her current position within the embedded GNSS 20a. The system 100 will then compute the most convenient path and will beneficially guide the driver 12 to the chosen site. Optionally, the parking-register device 27 includes GNSS 27a and internet 27b capabilities.

In another embodiment, a subscriber 24 can register the geographic earth location of at least one parking spot location 10b to the community-based transportation services network 15, wherein the parking spot location 10b is stored, entered or recorded into the parking inventory database 15c. Also, the subscriber 24 can either type the address of the place that he/she wants to register, or register it on the touchscreen map, or use GNSS receiver to register the geographic earth location of the parking spot where they are currently located or positioned. The GNSS receiver can be a GPS, GLONASS, Galileo, IRNSS, QZSS, or Beidou satellite receiver. Further, the subscriber 24 can register a parking-spot 10b by providing a name, address and/or picture of the parking facility corresponding to the at least one parking-spot.

Optionally, the community-based transportation services system 100 includes a user's communication device 12 (or the transportation-services device 2027) communicatively coupled to a community-based transportation services network 15; the community-based transportation services network 15 having a processor; a memory communicatively coupled to the processor, the memory comprising instructions that when executed by the processor performs operations comprising: monitoring the availability of parking-spots 10*a*/10*b* within a pre-selected radius/distance of a major event; monitoring the amount of traffic within the vicinity of the major event; recording and saving data associated with the parking-spots 10*a*/10*b* selected by the users 12 so that these parking-spots 10*a*/10*b* can be used at a later time by other users 12 of the system 100; providing taxi service pickup and/or delivery from the parking-spot 10*a*/10*b* selected by the user 12 to the major event or within the vicinity of the major event; and providing a discount to users 12 who use the system 100 to select an available parking-spot 10*a*/10*b* and then use the same system 100 to be taxied to the major event or taxied within a preselected range of the event, thereby allowing users 12 to avoid traffic jams normally located near a major event.

A further feature of the present invention, as shown in FIG. 1B, provides a method 200 and system 100 that utilizes a transportation-services device 2027 having a software application program 18/18*b* suitably arranged to allow a user 12 to select at least one parking-spot 10*a*/10*b* for rent when attempting to park a vehicle 11 and/or allow a user 24 to register at least one parking spot 10*b* with the community-based transportation services network 15 for allowing another user 12 to rent or pay a fee to park his or her vehicle 11 in the at least one parking-spot 10*a*/10*b*. In effect, the transportation-services device 2027 is arranged to carry out all the functions of both the user's communication device 20 and the parking-register device 27 in just one device 2027. Likewise, the system 100 of this embodiment includes the transportation-services device 2027 communicatively coupled to the community-based transportation services network 15 to establish the parking-spot communication link 17 (also referred to as a first communication link) and the parking-location registration link 23 (also referred to as a first communication link). The transportation-services device 2027 also includes a processor 2027*p* communicatively coupled to memory 2027*m* as shown in FIG. 1F. The memory and processor of this embodiment are external or internal to the device 2027.

In another embodiment, the community-based transportation services network 15 of the system 100 advantageously includes a community-based services processor 15*p* suitably configured to perform a predefined set of basic operations in response to receiving a corresponding basic instruction selected from a predefined native instruction set of codes. The community-based services processor 15*p* is communicatively coupled to a memory 15*m*. The memory 15*m* comprises instructions that when executed by the processor 15*p* performs operations comprising at least one set of machine codes selected from the native instruction set for executing a sequence of operations/functions/steps stored in the memory 15*m*. The resulting data from the executed functions/operations/steps are communicatively transmitted to the user's communication device 20, the parking-register device 27, the transportation-provider network 28, the biosensor collector 32 and/or the transportation-services device 2027, thereby enabling the objectives of the present invention to be carried out.

Optionally, the system 100 of the invention is highly adaptive in that it can include at least one camera and/or video camera that can provide live feedback for allowing a user 12 to visually see if parking is available. The at least one camera and/or video camera will be located at or near the parking spots for allowing users 12 to visually monitor parking availability.

Figure 2A:
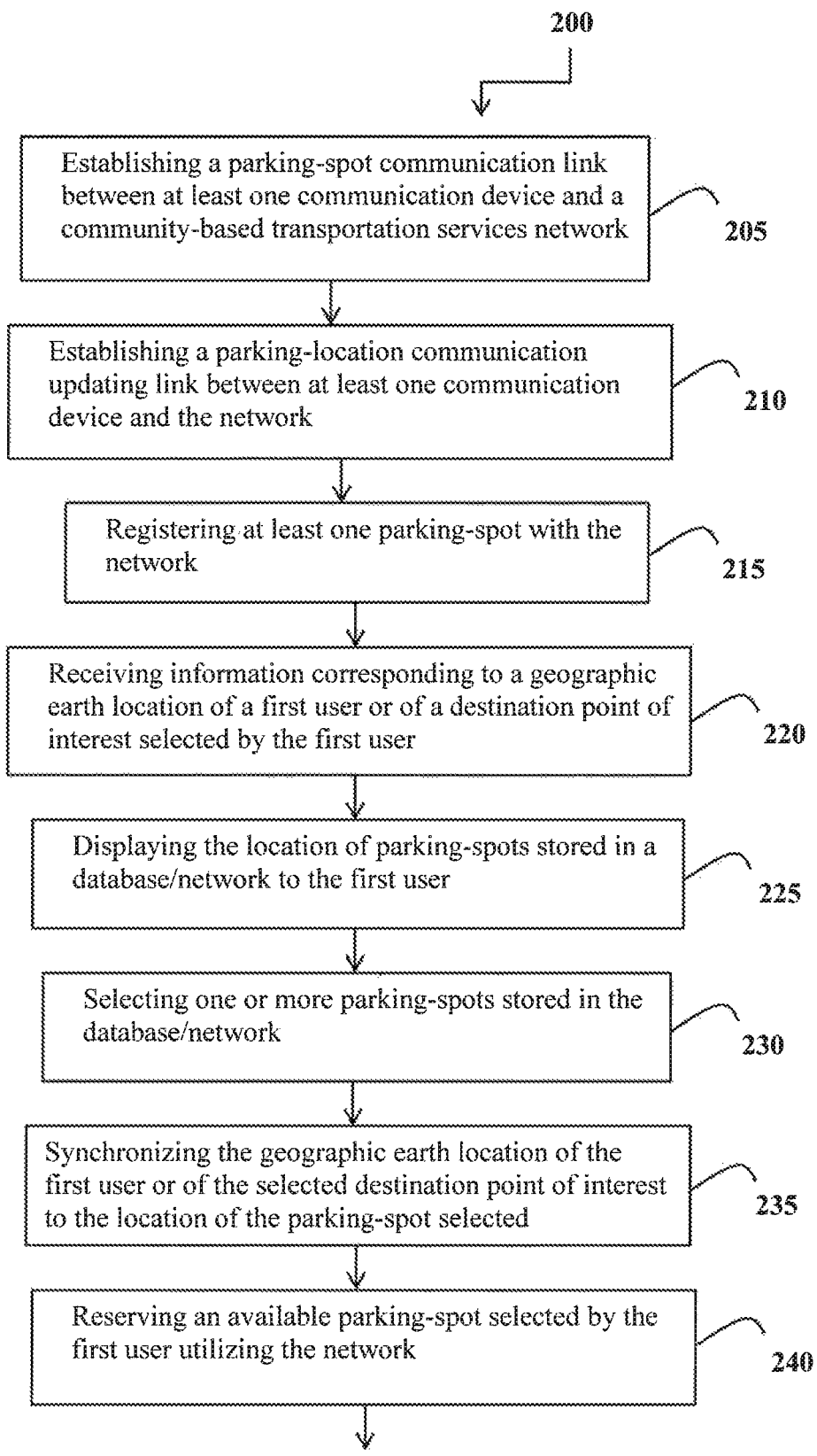
FIG. 2A represents an execution diagram for the method of managing and determining the location of parking-spots for a first user.

Referring now to FIG. 2A, one embodiment is directed to a method 200 of managing and determining the location of parking-spots stored in a parking inventory database 15*c* via one or more processors of the user's communication device 20 or the transportation-services device 2027. The method 200 includes the step of 205 establishing a parking-spot communication link 17 between a user's communication device 20 or transportation-services device 2027 and a community-based transportation services network 15. The method also incorporates the step of 220 receiving information corresponding to determining a geographic earth location of a first user 12 or of a destination point of interest 21 selected by the first user 12. Another step of 225 the method includes the step of providing or displaying 25 the location of parking-spots to the first user 12. The parking-spots will be located within a preselected radius 25 of the geographic earth location of the first user 12 or of the destination point 21 selected by the first user 12.

Referring still to FIG. 2A, the method 200 additionally includes the step of 230 selecting one or more parking-spots stored in the parking inventory database 15*c* for allowing the first user 12 to park his or her vehicle 11. A further step of the method encompasses the step of 235 synchronizing the geographic earth location of the first user 12 or of the selected destination point of interest 21 to the location of the parking-spot selected by the first user 12. Likewise, the method of the present invention further incorporates the step of 265 providing directions 25 to the first user 12 corresponding to the parking spot selected by the first user 12.

In a further embodiment of the present invention, the method 200 comprises the step of 210 establishing a parking-location registration link 23 between a parking-register device 27 (or transportation-services device 2027) and the community-based transportation services network 15 (See FIGS. 1A, 1B and 2A). The user's communication device 20, the parking-register device 27 and the transportation-services device 2027 include a software application program 18 configured to manage, register and determine the location of parking-spots. The method 200 also includes the step of, a second user 24, registering 215 at least one parking spot 10*b* with the community-based transportation services network 15. The at least one parking spot is stored in the database 15*c*. The database 15*c* is communicatively coupled to the network/cloud 15*b*, which allows the first user 12 to advantageously rent or pay a fee to park his or her vehicle 11 in a parking spot stored in the parking inventory database 15*c*.

Figure 2B:
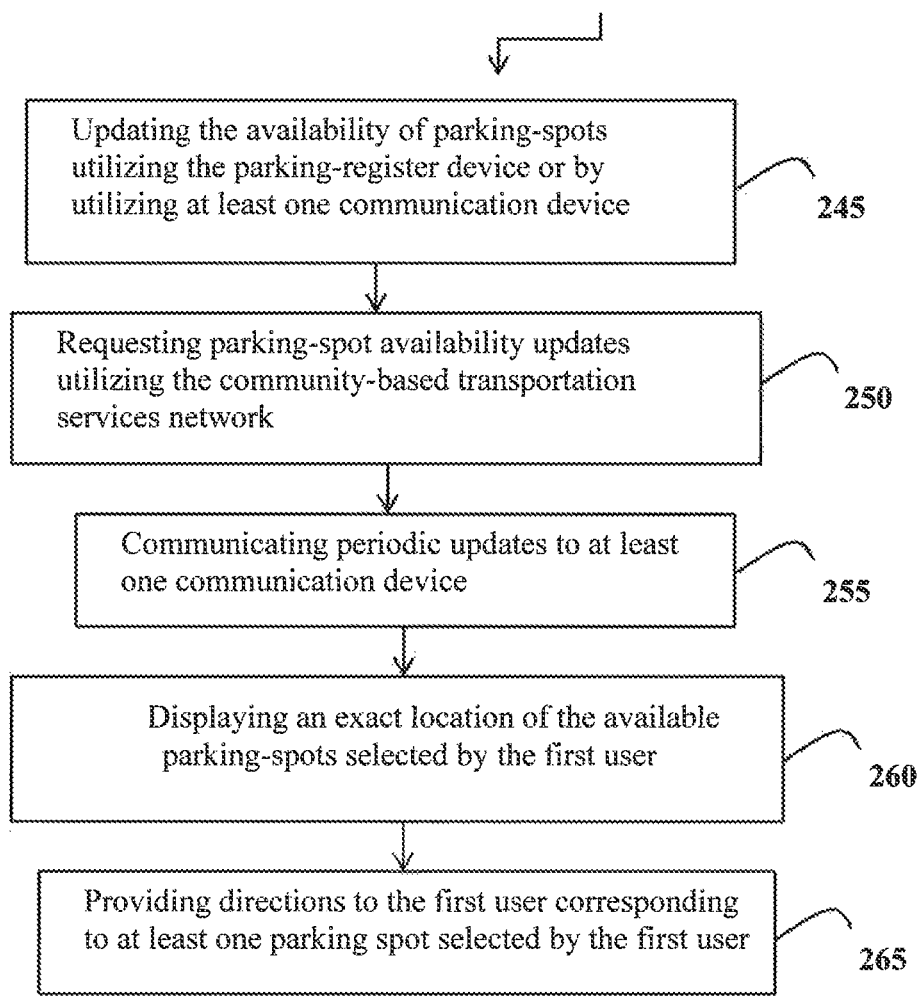
FIG. 2B is a continuation of FIG. 2A.

Optionally, the method 200 includes the steps of 240 reserving an available parking-spot selected by the first user 12 utilizing the community-based transportation services network 15 and/or the communication device 20 (or the transportation-services device 2027); updating 245 the availability of parking-spots using the parking-register device 27 (or the transportation-services device 2027) or by utilizing the communication device 20; requesting 250 parking-spot availability updates utilizing the community-based transportation services network 15 and/or the communication device 20 (or the transportation-services device 2027); wherein requesting parking-spot availability updates 250 includes the community-based transportation services network 15 communicating 255 periodic updates to the communication device 20 (or the transportation-services device 2027) and displaying 260 an exact location 25 of the available parking-spots selected by the first user 12 (See FIGS. 1A, 1B, 2B and see also block 670).

Figure 3:
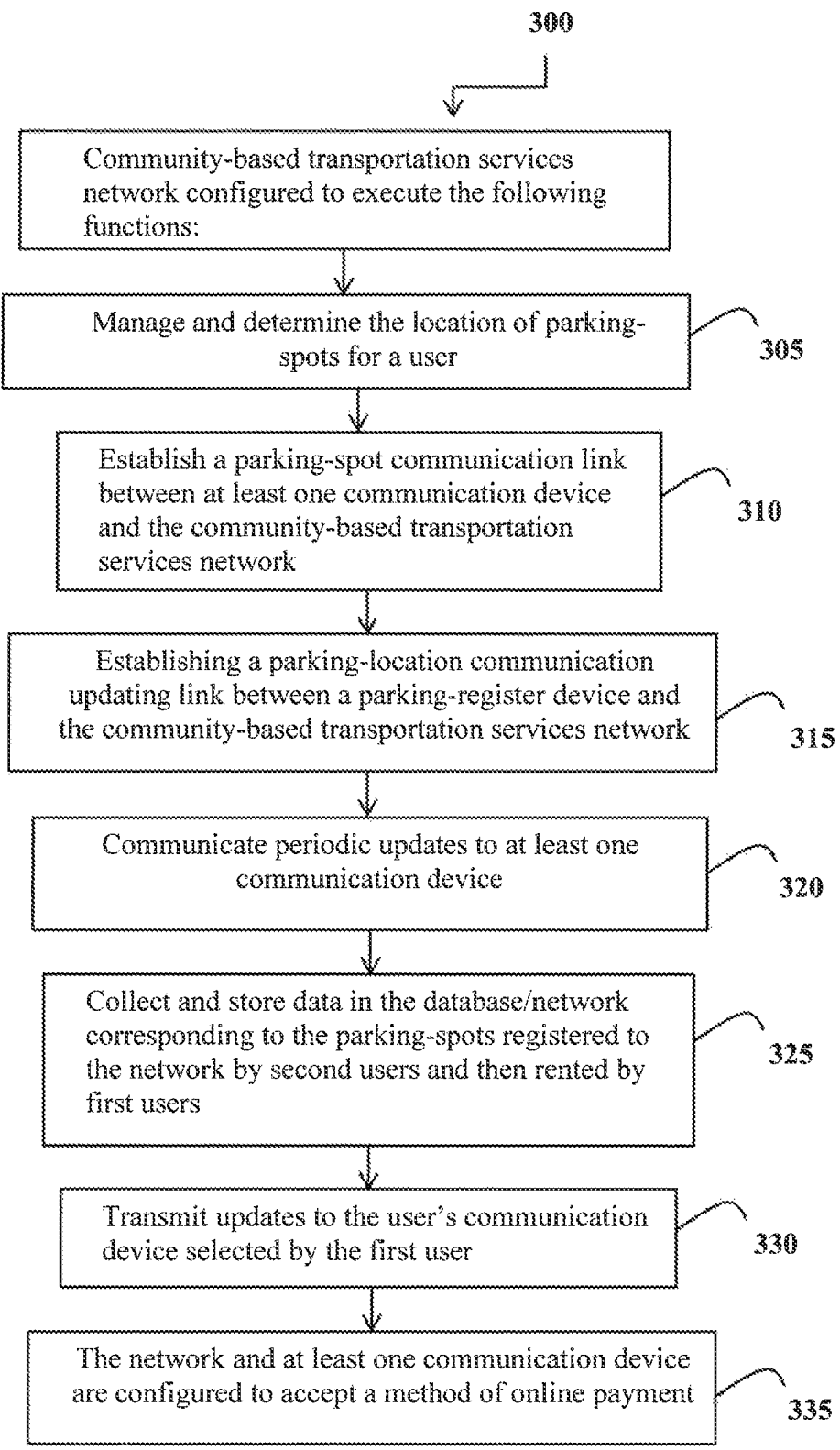
FIG. 3 represents a process diagram showing the specific functions/operations that are executed by the community-based transportation services network.

Referring now to FIG. 3, a process diagram 300 is represented showing some of the specific functions that are executed by the community-based transportation services network 15. For instance, the community-based transportation services network 15 is highly adaptive in that it is able to execute the following comprehensive functions: manage 305 and determine the location of parking-spots for a first user 12; establish 310 a parking-spot communication link 17 between a communication device 20 (or the transportation-services device 2027) and the community-based transportation services network 15; establish 315 a parking-location registration link 23 between a parking-register device 27 (or the transportation-services device 2027) and the community-based transportation services network 15; communicate 320 periodic updates 25 to the communication device 20 (or the transportation-services device 2027); transmit 330 updates 25 to the first user's 12 communication device 20 (or the transportation-services device 2027) such as parking expiration warnings, receipt for services ordered, parking expiration violations; and a 335 method of payment accepted for allowing a first user 12 to conveniently park his or her vehicle 11 (See also FIG. 6A).

Figure 6A:
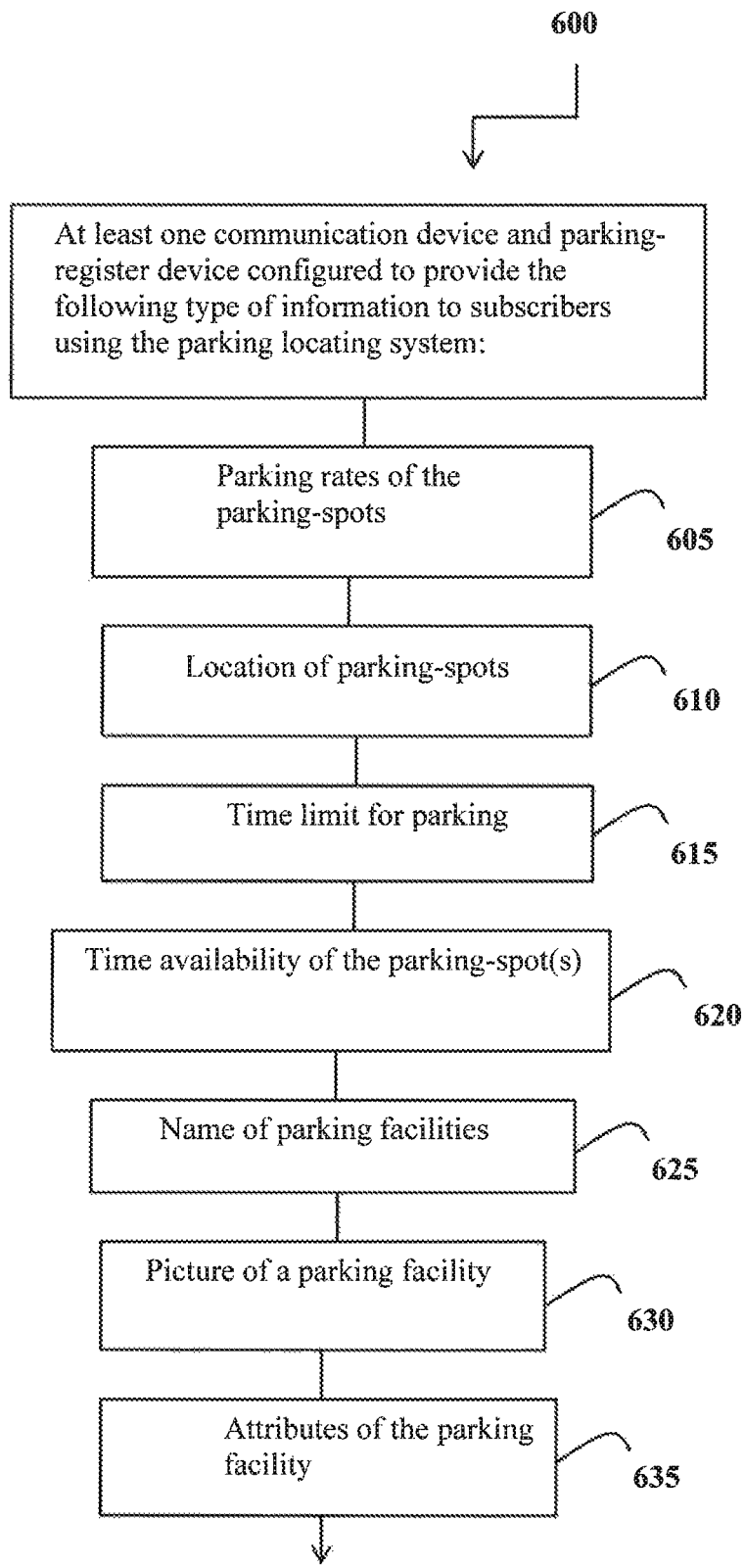
FIG. 6A represents an execution diagram demonstrating the type of information that the user's communication device, parking-register device or transportation-services device provides to subscribers.
Figure 6B:
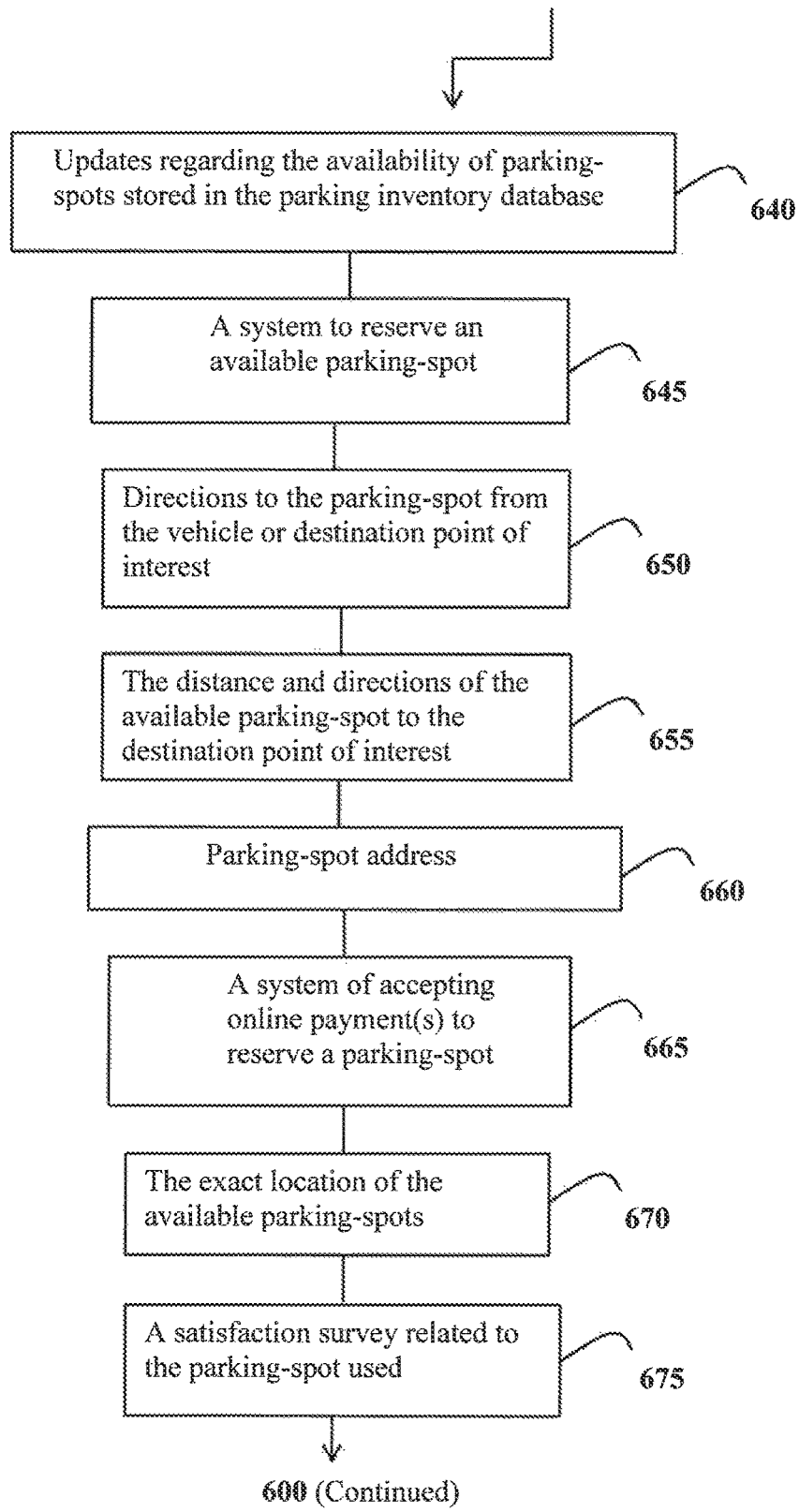
FIG. 6B is a continuation of FIG. 6A.
Figure 6C:
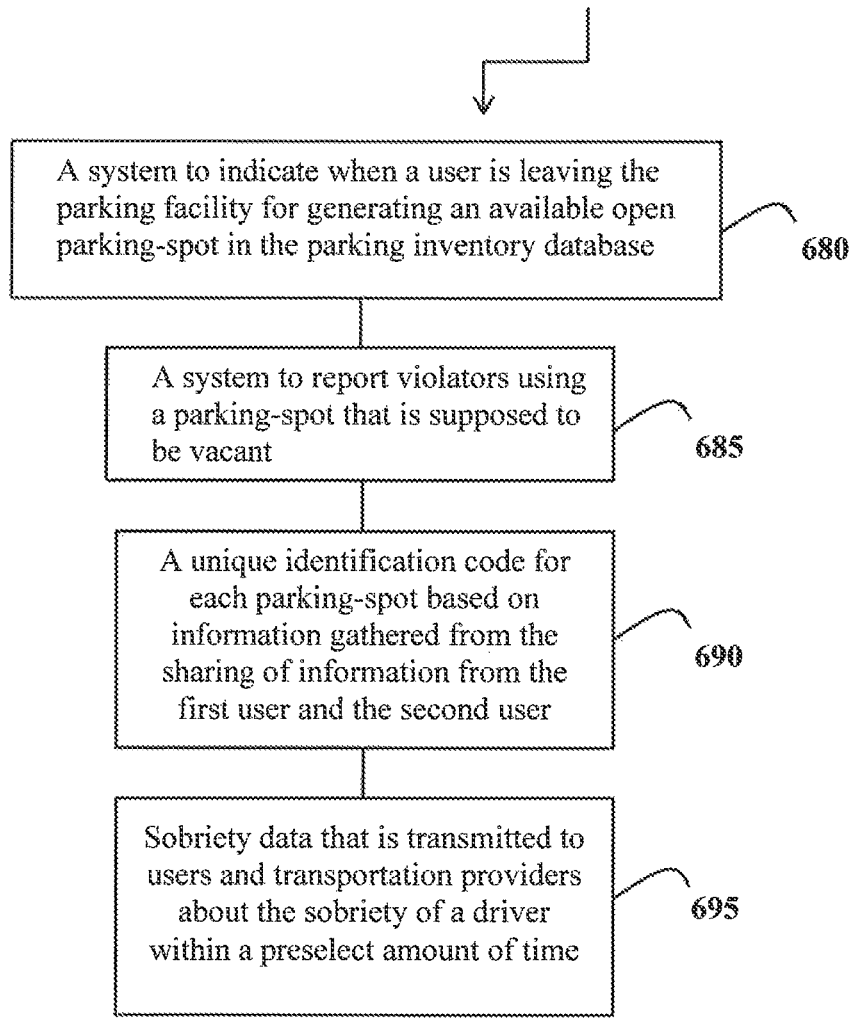
FIG. 6C is a continuation of FIG. 6B.

Referring still to FIG. 3, the community-based transportation services network 15 is configured to execute the following additional functions: collect and store data 325 corresponding to parking-spots available on a parking inventory database 15c, display or determine the following functions: location of parking-spots, destination addresses, current location of the vehicle 11 or the mobile device 20 (or the transportation-services device 2027), departure time, vehicle identification information, parameters related to the surrounding or infrastructure of a parking-spot, the distance of the available parking spots from the first user's vehicle 11 or mobile device 20 (see also block 655), the distance of the available parking spot(s) from the first user's destination address (see also block 655), parking rate(s) for each available parking spot, parking spot's address or other guiding information (see block 660), departure time or any other restricting information regarding the parking of a vehicle 11 in said parking spot(s), and a unique identification code for each parking spot based on information gathered from the sharing of information from users (i.e., first and second users) using the application program 18 or other application programs (See also FIGS. 6A, 6B, 6C and block 690). Importantly, the application programs 18 referenced-above can be offered by business establishments in the travel and/or transportation industry, technology industry, or service and luxury industry for other types of communication devices that provide drivers with directions to specific destinations of interest (see also block 655 and FIG. 6B).

Figure 4A:
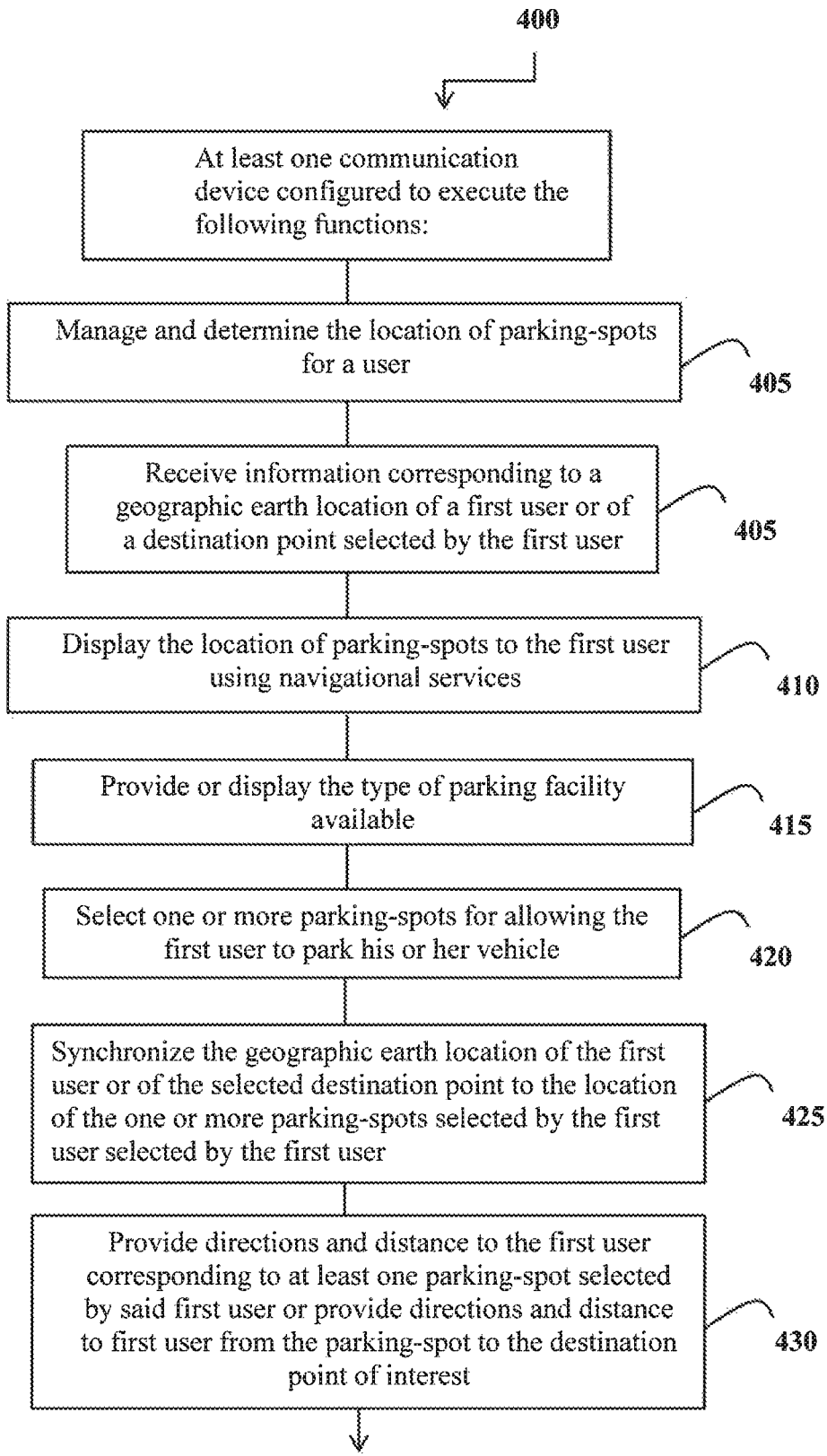
FIG. 4A represents another process diagram showing the specific functions/operations that are executed by the user's communication device or the transportation-services device for one embodiment of the present invention.
Figure 4B:
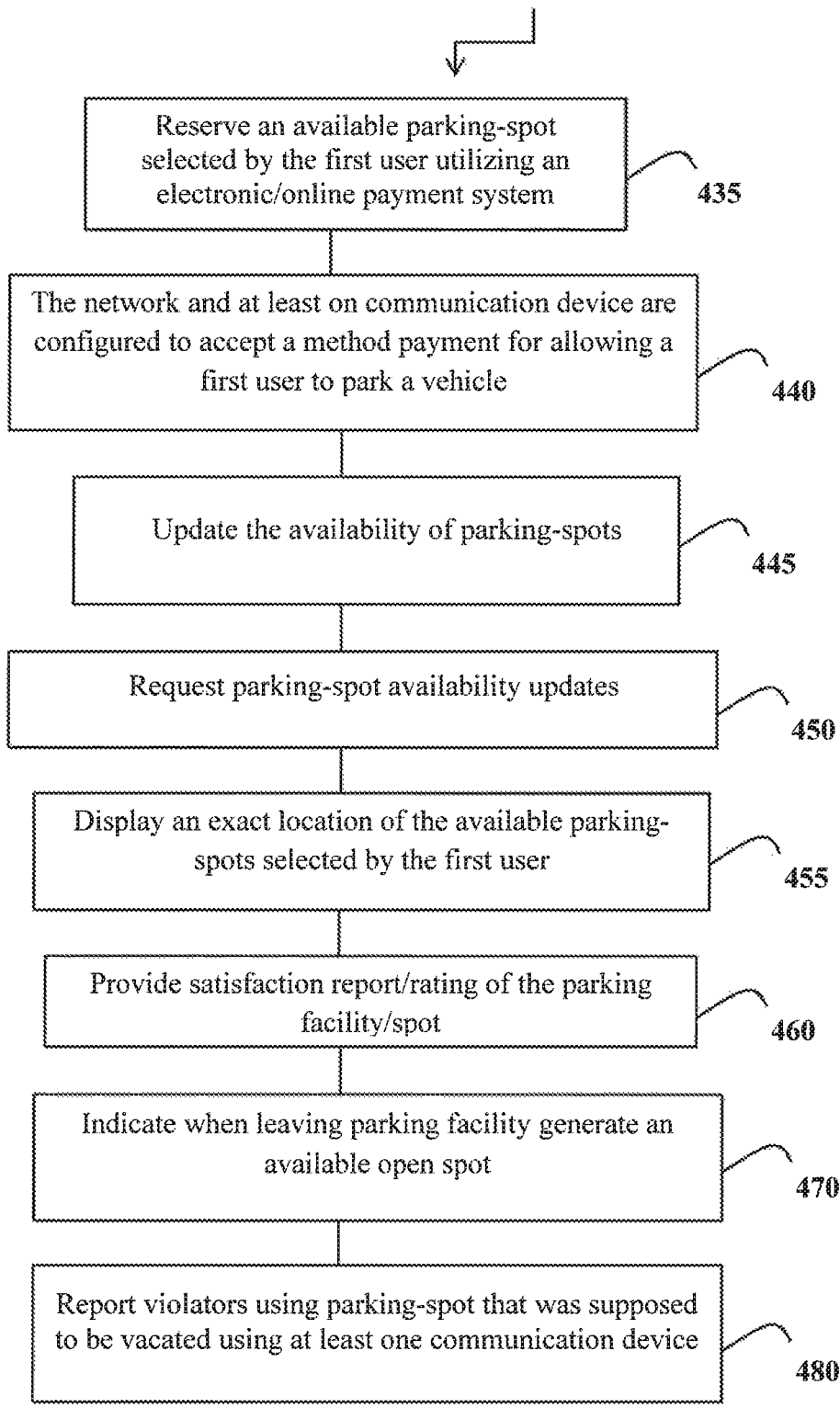
FIG. 4B is a continuation of FIG. 4A.

Referring now to FIG. 4A, another process diagram 400 is represented showing some of the specific functions that are executed by the user's communication device 20 (or the transportation-services device 2027). In use, the communication device 20 (or the transportation-services device 2027) is highly adaptive in that it is able to execute the following beneficial functions: receive 405 information in real-time or non-real-time corresponding to a geographic earth location of a first user 12 or of a destination point of interest 21 selected by the first user 12; provide or display 410 the location of parking-spots to the first user 12 using navigational services such as, but not limited to GNSS; provide or display 415 the type of parking facility available; select 420 one or more parking-spots for allowing the first user 12 to park his or her vehicle 11; synchronize 425 the geographic earth location of the first user 12 or of the selected destination point 21 to the location of the one or more parking-spots selected by the first user 12; provide 430 directions and distance to the first user 12 corresponding to at least one parking-spot selected by said first user 12 or suitably configured to provide the first user 12 directions and distance from the parking-spot selected by the first user 12 to the destination point of interest 21 selected by the first user 12, and reserve 435 an available parking-spot selected by the first user 12 utilizing an electronic/online payment system (see also block 645).

Referring still to FIG. 4A, a process diagram 400 shows some additional functions that are executed by the communication device 20 (or the transportation-services device 2027). For instance, the communication device 20 (or the transportation-services device 2027) is highly adaptive in that it is able to execute the following additional beneficial functions: the community-based transportation services network 15 and the communication device 20 (or the transportation-services device 2027) are configured to perform 440 a payment method that allows a first user 12 to park a vehicle 11; update 445 the availability of parking-spots; request 450 parking-spot availability updates; display 455 an exact location of the available parking-spots selected by the first user 12; provide 460 the first user 12 with the ability to participate in a satisfaction report/rating survey related to the parking facility/spot used (see also block 675); indicate 470 when a user 12 is leaving the parking facility to generate an available open spot 10a/10b (see block 680); transmit sobriety data to users and transportation providers about the sobriety of a driver within a preselect window/amount of time, and report 480 violators using a parking-spot that is supposed to be vacant (See also FIG. 6A and block 685).

As shown in FIG. 5, a process diagram for the present invention shows the type of functions that are to be executed by the parking-register device 27 (or the transportation-services device 2027). In use, the parking-register device 27 (or the transportation-services device 2027) is suitably configured to execute the following beneficial functions: provide 505 parking-spot locations (see also block 610), directions (see block 650), available parking spaces, cost to park (see block 605), time limit for parking (see block 615), time availability (see block 620), name of parking facilities (see block 625), a picture of parking facility (see block 630), attributes of the parking facility (see block 635), and actions that may be taken by the user 12/24 with respect to the parking facility/spot; update 510 the availability of parking-spots (see also block 645); accept 515 electronic/online payments to allow a user 12 to reserve parking-spot (see block 665); the community-based transportation services network 15 and the parking-register device 27 (or the transportation-services device 2027) are configured to perform 520 a method of payment for allowing a user 12 to park a vehicle 11; a sensing 530 means for providing information in real-time regarding the availability of said parking spots, the sensing means 530 can include an underground sensor (one for each parking lot) that indicates whether a vehicle 11 is parked in a space, the sensor 530 being wireless or hardwired, fastened to the pavement and adjacent to each parking spot; and the sensing means 530a can be an imaging device thereby allowing said system to be used as an alert mechanism in case of a theft attempt or to send an alert message that includes an updated digital photo of the parked vehicle 11 (See also FIG. 6A).

In an alternative embodiment, the present invention is highly adaptive in that it can store parking-spot locations for jurisdictions/localities in a smart database 15c based on historical data input by the subscribers 12/24. The database 15c is advantageously configured to be smart in that it allows the subscribers 12/24 to share information about potentially available parking-spots based on spots that were historically registered into the system 100 or based on spots that were historically used by subscribers 24. This sharing of information allows the system 100 to generate an inventory of potentially available parking-spots by allowing subscribers to verify the existence or non-existence of potentially available parking-spots for use/rent or by the recognition of historical data based on the use of parking-spots. Moreover, the inventory of potentially available parking-spots will acquire a geographic earth location when a subscriber 12/24 enters an address, registers an address on a touchscreen map or a GNSS receiver configured to register the geographic earth location of the parking spot. Further, the smart database 15c will be available for use in real-time or non-real-time depending on whether the parking-spot registered has real-time availability capabilities or if the user/subscriber 12 is just pre-planning a trip and is not in need of real-time information.

Figure 7:
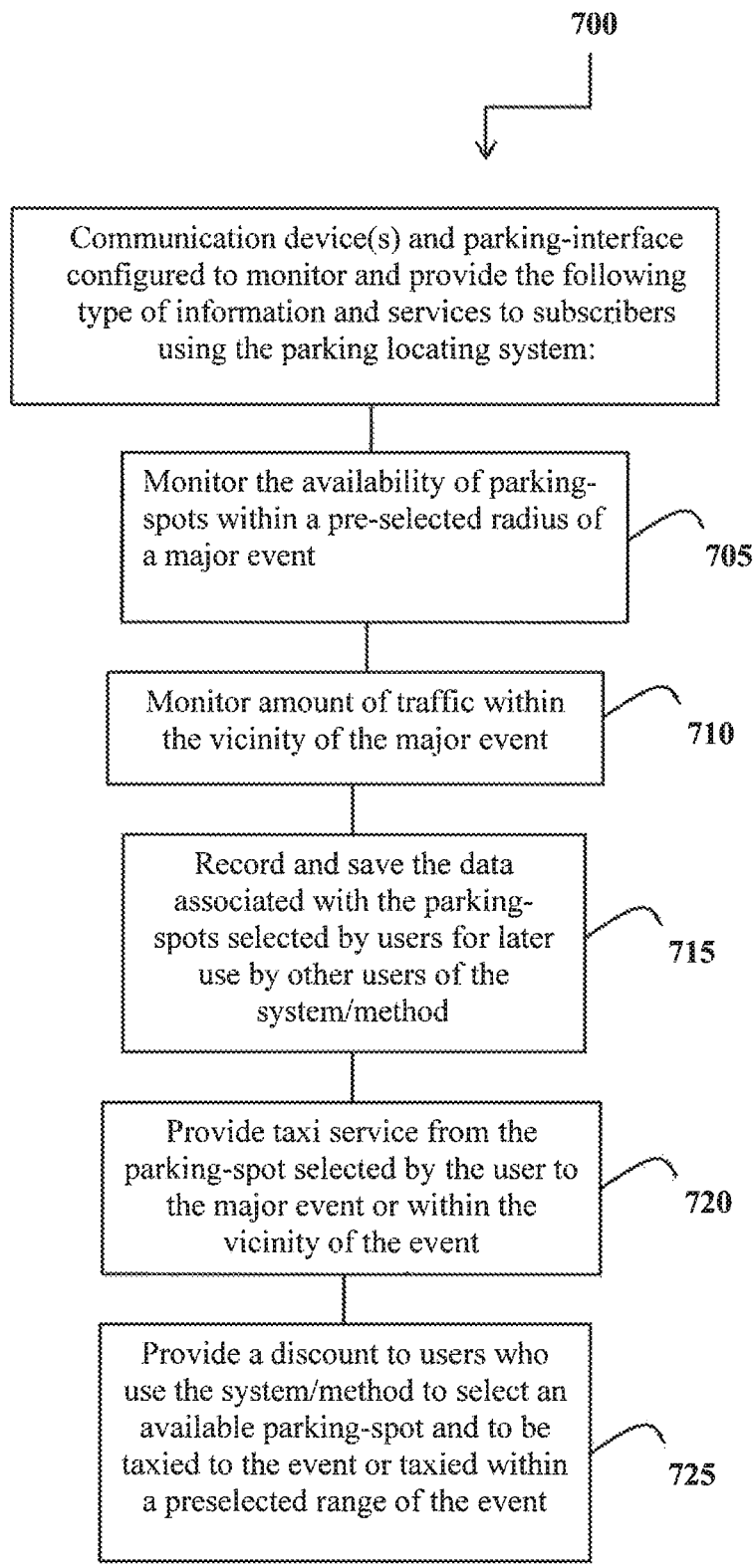
FIG. 7 represents an execution diagram for monitoring and providing information and services to subscribers when using the community-based transportation services system to attend and park at a pre-selected distance from a venue/location hosting a major event.

In a further embodiment, the present system and method are configured, as shown in FIG. 7, to monitor and provide information and services to a subscriber's device (See FIGS. 1A and 1B) when using the community-based transportation system 100 to attend major events. The method and system of this and all other embodiments of the present invention, can advantageously be executed by one or more processors. In this disclosure, major events refer to, but is not limited to, concerts, sporting events, fund raisers, charity events, religious events, museum events, social events, business events, and various functions/events held at a venue.

At block 705, the process of the present invention includes the step of monitoring the availability of parking-spots within a pre-selected radius/distance of a major event. This feature allows users to avoid the high prices charged by most event parking facilities. This feature also allows users to avoid major traffic jams associated with most major events. This feature additionally helps cities to avoid major traffic from being saturated within an event location/venue. This feature further helps residential areas located near an event location since the community-based transportation services system allows users attending a major event to find parking-spots in other areas that are not congested by traffic from the major event.

At block 710, the process is configured to include the step of monitoring the amount of traffic within the vicinity of the major event. A user can then optionally select a parking-spot located within a pre-selected distance of the major event which advantageously allows the user to find a parking-spot in an area that is not congested or saturated by the event traffic. Importantly, this feature can control the amount of event traffic generated by users choosing to park away from the major event which can help to avoid traffic jams.

At block 715, the process is configured to include the step of recording and saving data associated with the parking-spots selected by users so that these parking-spots can be used later by other users of the system/method. In essence, this feature allows other users to possibly reuse these available parking spots for other events held at the event facility/venue. Further, this feature allows users to offer their parking spots for rent/use which puts land and space to its best use. Alternatively, block 715 can notify other users of parking-spots historically used for upcoming major events that are within a preselected distance/radius of the hosting facility/venue.

At block 720, the process is comprised of the step of advantageously providing taxi service pickup and/or delivery from the parking-spot selected by the user to the major event or within the vicinity of the major event. This feature advantageously puts land and available space to its best use while dispersing traffic in such a way that can reduce traffic congestion since parking needs are spread out over a specific locality.

At block 725, the process is configured to include the step of providing a discount to users who use the system/method to select an available parking-spot and then use the same system/method to be taxied to and from the major event or taxied within a preselected range of the event which allows users to avoid traffic jams normally located near a major event.

In a further embodiment, the community-based transportation services network 15 of the system 100 includes at least one community-based services processor 15p configured to perform a predefined set of basic operations in response to receiving a corresponding basic instruction selected from a predefined native instruction set of codes. The at least one community-based services processor 15p is communicatively coupled to a community-based memory 15m. The memory 15m comprises instructions that when executed by the at least one processor 15p performs operations/functions/steps comprising at least one set of machine codes selected from the native instruction set for executing a sequence of operations/functions/steps of the method 200 and system 100 that are stored in the memory 15m. The resulting data from the executed functions/operations/steps are communicatively transmitted to the user's communication device 20, and/or the parking-register device 27, an/or the transportation-provider network 28, and/or the biosensor collector 32a and/or the transportation-services device 2027, thereby enabling the objectives of the present invention to be carried out.

4. Method and System to Monitor and Determine the Sobriety of Transportation Drivers:

FIGS. 1A, 1B and 1D refer to another embodiment of the present invention depicting the components of the system 100 configured to allow a first user 12 or transportation provider 13b to monitor and determine the sobriety of a transportation driver 13. For instance, the system 100 includes a biosensor collector system 32 communicatively coupled to the community-based transportation services network 15 and/or to the communication device 20 (or the transportation-services device 2027) and/or to the transportation-provider network 28 for establishing a sobriety-monitoring communication link 17b (also referred to as a second communication link). The sobriety-monitoring communication link 17b is configured to receive information in real-time or non-real-time from the biosensor collector system 32. Optionally, the biosensor collector system 32 and/or transportation provider 13b will have a software application program 18b configured to monitor and determine the sobriety of a transportation driver 13. Alternatively, the communication device 20 (or the transportation-services device 2027) will also include GNSS 20a and internet 20b capabilities.

Figure 8:
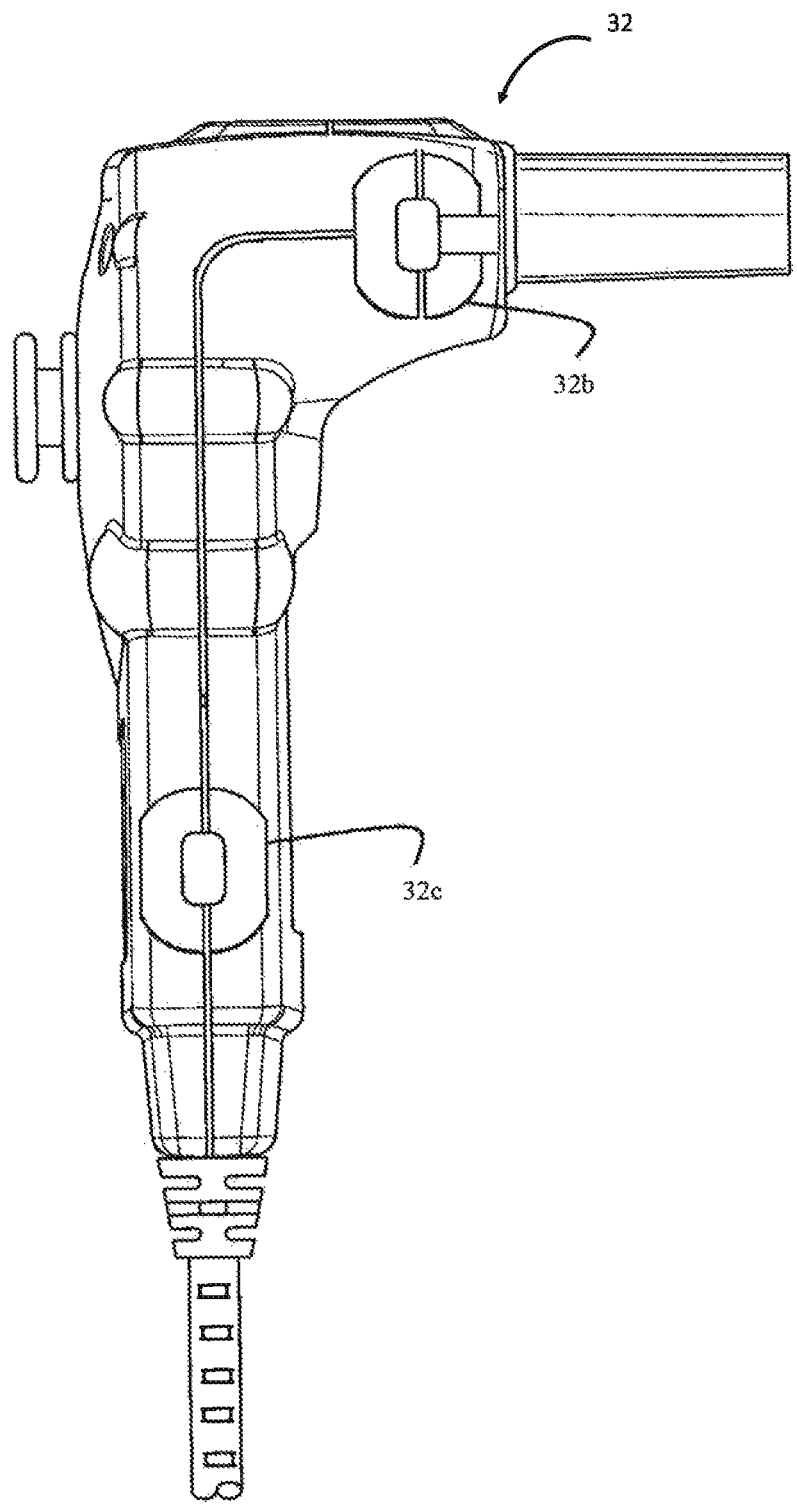
FIG. 8 is directed to a biosensor collector device.

Referring now to FIG. 8 of the present invention, a biosensor collector device 32 (or 32a) has a DNA sensor 32b and an intoxication substance sensor 32c that is configured to allow a consumer 12/12d using a communication device 20 (or the transportation-services device 2027) having a mobile transportation/taxi app 18b (e.g., UBER. LYFT or MOOVN app) to determine if it is safe or not to use the services of the transportation/taxi provider 13b (e.g., UBER.

LYFT or MOOVN). This beneficial information/data will be available to consumers 12/12d via the sobriety-monitoring communication link 17b (or second communication link 17b).

In use, after a driver/consumer 12 (i.e., also a consumer 12d) finds a parking spot, the driver/consumer 12/12d may now want to use the services of a transportation/taxi provider 13b in order to be transported to a destination point of interest 21. However, the deciding factor for a consumer 12d regarding which transportation provider 13b to use could be predicated on whether the provider 13b has a mobile transportation/taxi app 18b that includes a method and/or system to allow consumers 12d to verify a potential transportation driver's 13 identity (e.g., UBER, LYFT or MOOVN driver) and sobriety. Importantly, the transportation/taxi app 18b or a separate app on the consumer's 12d communication device 20 (or the transportation-services device 2027) is configured to detect a driver's 13 intoxication level within a preselect length of time with respect to various illegal drugs and/or alcohol and then this information is transmitted to the consumers/drivers 12/12d via the sobriety-monitoring communication link 17b.

Referring still to FIG. 8, the method and system is configured to monitor and determine the sobriety of transportation/taxi drivers 13 which is available to the transportation/taxi providers 13b via the sobriety-monitoring communication link 17b (or second communication link 17b). This information will allow transportation providers 13b (e.g., MOOVN, UBER or LYFT) to monitor the sobriety of its drivers 13 for a predetermined amount/length of time. For example, the transportation providers 13b could require its drivers 13 to submit to a test every hour by providing a saliva and/or condensate sample from air exhaled by said drivers. This type of testing would allow the transportation providers 13b to ensure the safety of its consumers 12/12d and help to maintain a positive company/brand image by monitoring the sobriety of its drivers 13. Similarly, this type of monitoring could help transportation providers to reduce their insurance rates and claims since they would be able to eliminate drivers who fail to maintain their sobriety and/or deter potential drivers from applying to their company for employment who are not willing to meet stringent sobriety standards in the transportation/taxi industry. Optionally, the transportation providers 13b could make this information available via its network 28 to its consumers 12/12d (via the second communication link 17b) so that they could make a well-informed decision when selecting a transportation provider 13b.

In use, the biosensor collector 32a receives a saliva sample or a condensate sample from air exhaled by the potential transportation driver 13. In the sample(s) collected, there are cells or cell fragments which contain DNA corresponding to the potential transportation driver 13. Analysis of this DNA can be used for identification and recognition of the driver 13. Hence, it is possible to ascertain and/or verify the identity of a transportation driver 13 by comparing the DNA sample collected from the human cells in the saliva sample or the exhaled air condensate sample to a corresponding DNA profile corresponding to the driver 13. This DNA profile and corresponding information is stored in a DNA profile database 15c and/or stored in the parking inventory database 15c. In essence, the biosensor collector 32a allows a potential transportation driver 13 to provide a sample containing DNA in order to see if it matches the potential transportation driver's 13 DNA profile stored in the database 15c for identification verification purposes. Importantly, verification of the potential driver 13 by DNA matching prevents potential drivers 13 from using some random person to provide the necessary samples to the biosensor collector 32a (also 32) for determining the identity and sobriety of the driver 13.

In use, and as previously discussed in this disclosure, the intoxication substance sensor 32c of the biosensor collector 32a is suitably configured to sense and/or detect the presence of illegal intoxicating drugs/substances and alcohol in the system of a potential transportation driver 13 after their identity has been identified through DNA verification. Likewise, the intoxication substance sensor 32c is configured to advantageously analyze the sample provided by the potential transportation driver 13 to determine and/or detect if the driver's 13 sample is below a pre-determined intoxication level or threshold for drugs and/or alcohol.

In an alternative embodiment of the present invention, the biosensor collector device 32 is configured to function/operate with just an intoxication substance sensor 32c (i.e., no DNA sensor). In this embodiment, a user 12 could require a driver 13 to submit to a sobriety check/analysis if the driver's 13 sobriety has not been validated within a preselected amount of time (e.g., one hour) without the need of having to use a DNA sensor 32b. Once the driver's 13 sobriety has been validated, the results and time period for this test is registered to the system 100 and viewable by users 12 and transportation providers 13b. Further, the user's 12 identity (i.e. user who requested and verified the sobriety test) could be registered and recorded to the system 100 for additional verification purposes and made available to other users 12 and transportation providers 13b. In this embodiment, a driver 13 could also submit to a sobriety check/analysis via a dash-cam video or via any other type of video recording device which would help to validate who is submitting sobriety testing. The sobriety check/analysis would be recorded and registered to the system 100 so that the results could be advantageously viewed and verified by users 12 and transportation providers 13b.

The results for verifying a potential transportation driver's 13 identity and intoxication level for drugs/alcohol can be made available to a consumer's 12/2d communication device 20 (or the transportation-services device 2027) for allowing the consumer 12/12d to see if the potential transportation driver 13 is sober or not. Similarly, the results for verifying a potential transportation driver's 13 identity and intoxication level for drugs/alcohol can be made available to the transportation/taxi providers 13b to allow them to determine if the potential transportation driver 13 is sober or not. Further, the intoxication substance sensor 32c of the biosensor collector 32a (also 32) can also be configured to function on a consumer's 12/12d communication device 20 for detecting if the potential transportation driver 13 is sober or not.

Optionally, the DNA sensor 32b can be an optical, electrical or microgravimetric DNA biosensor. Depending on the way in which the DNA sensor 32b is equipped, the subsequent cell disruption, the PCR (polymerase chain reaction), hybridization and the detection by fragment analysis of the DNA may be carried out directly on a chip or chip card (i.e., on a so-called "lab on a chip"). Alternatively, the DNA sensor 32b could also be configured to use a DNA fragment analysis method that is carried out by capillary electrophoresis or by Southern blot analysis.

In a further embodiment, the intoxication substance sensor 32c is suitably configured to detect the presence of intoxicating substances through biological signals through skin contact, vapor sampling, hair sampling, fingernail or toenail sampling/contact and/or saliva sampling.

In an additional embodiment of the present invention, the necessary samples are provided by a potential driver 13 in one simultaneous delivery to the biosensor collector 32a. In effect, the potential transportation driver 13 cannot provide one separate sample to verify his or her identity and then provide another separate sample using a random person who is not intoxicated in order to circumvent the testing results of the system.

Alternatively, a biosensor device is configured to monitor the sobriety of a transportation driver 13. The system is comprised of a biosensor collector device 32 communicatively coupled to a community-based transportation services network 15. The community-based transportation services network 15 includes at least one community-based processor 15p and the biosensor 32 includes a at least one biosensor processor 32p as shown in FIGS. 1C and 1D (the processors are internal or external to the devices). A community-based memory 15m is communicatively coupled to the community-based processor 15p and a biosensor memory 32m is communicatively coupled to the at least one biosensor processor 32p (the memories are internal or external to the devices).

Figure 10:
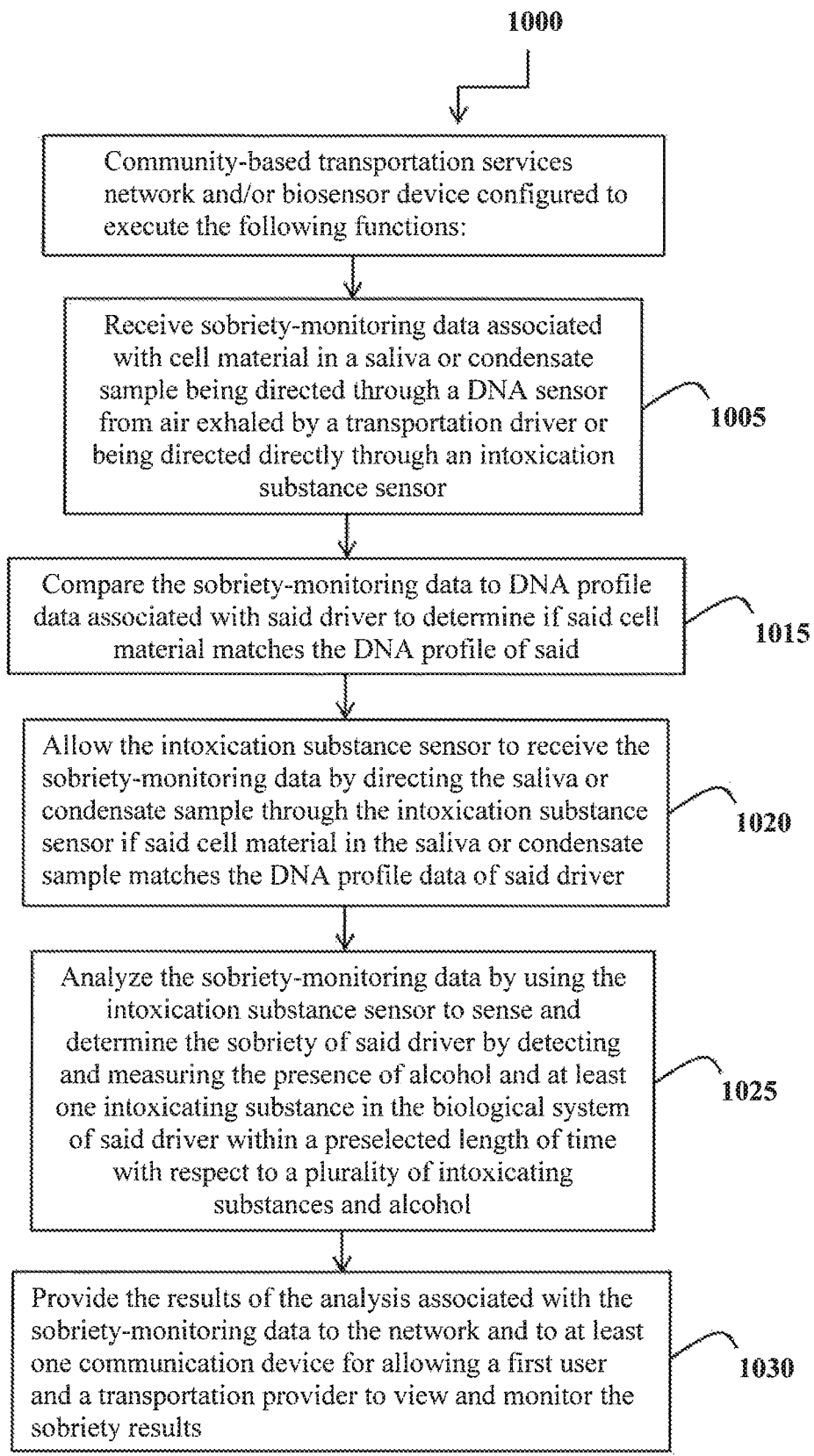
FIG. 10 represents a process diagram showing the specific functions/operations that are executed by the biosensor device and network.

The memory 15m/32m of the system is comprised of instructions that when executed by the processor 15p/32p performs operations comprised of: receiving 1005 sobriety-monitoring data associated with cell material in a saliva or condensate sample being directed through a DNA sensor 32b from air exhaled by a transportation driver, the DNA sensor 32b is communicatively coupled to the biosensor collector device 32; comparing 1015 the sobriety-monitoring data to DNA profile data associated with the transportation driver 13 to determine if said cell material matches the DNA profile of the transportation driver 13 for verifying the identification of said driver, the DNA profile data being stored in the memory of the community-based transportation services network 15; allowing 1020 the intoxication substance sensor 32c to receive the sobriety-monitoring data by directing the saliva or condensate sample through the intoxication substance sensor 32c if said cell material in the saliva or condensate sample matches the DNA profile data of the transportation driver, the intoxication substance sensor 32c being communicatively coupled to the biosensor collector device 32; and analyzing 1025 the sobriety-monitoring data by using the intoxication substance sensor 32c to sense and determine the sobriety of the transportation driver 13 by detecting and measuring the presence of alcohol and at least one intoxicating substance in the biological system of said driver (See also FIG. 10).

Optionally, the biosensor device includes memory 15m/32m further including instructions that when executed by the processor 15p/32p performs operations comprising: using the intoxication substance sensor 32c to analyze 1025 the sobriety-monitoring data by determining and measuring the intoxication level of said driver within a preselected length of time with respect to a plurality of intoxicating substances and alcohol; and providing 1030 the results of the analysis associated with the sobriety-monitoring data to the network 28 and to the transportation-services device 2027, thereby enabling the first user 12 and a transportation provider 13b to view and monitor the sobriety results/data 695 of said driver (See also FIG. 10).

Figure 9:
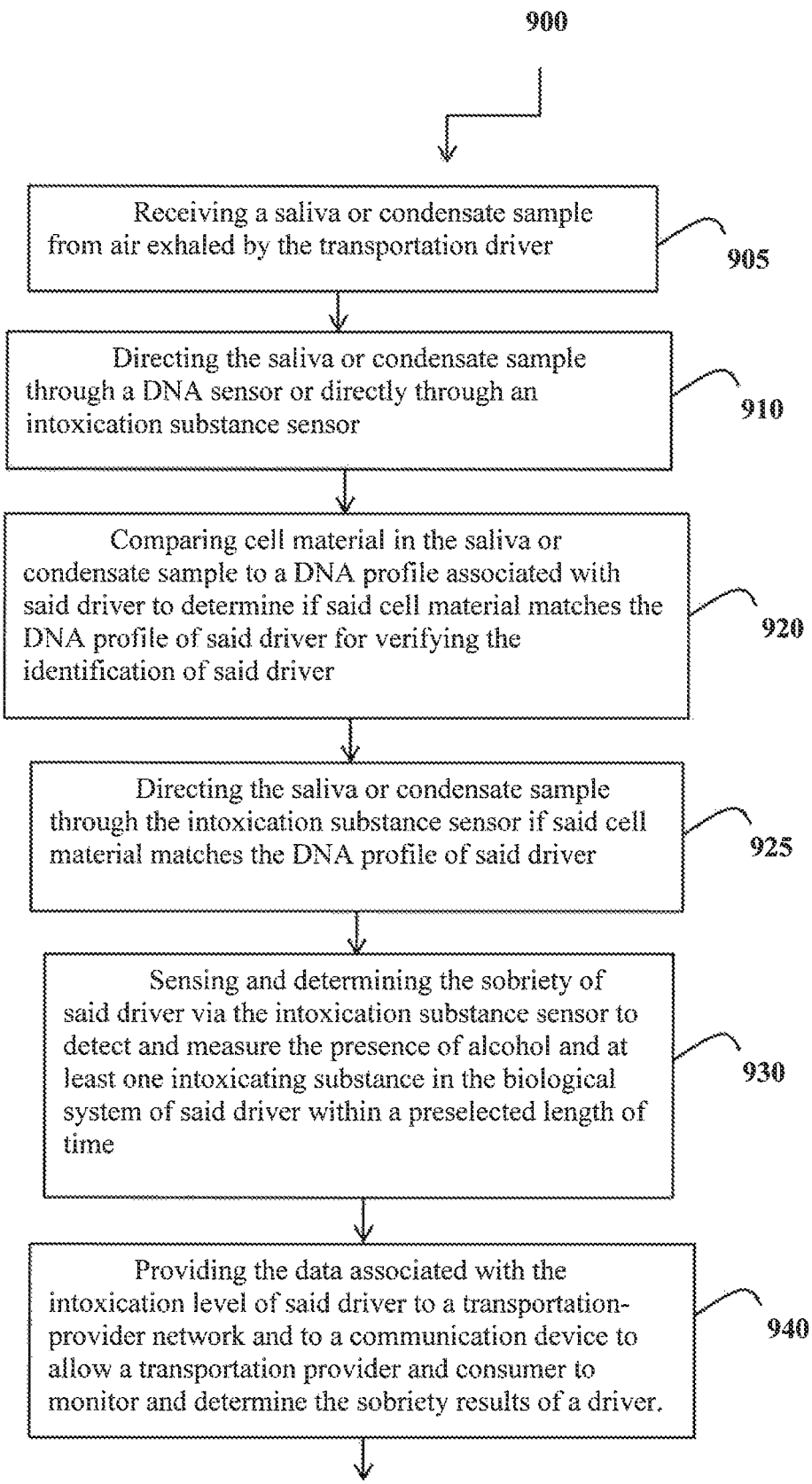
FIG. 9 represents an execution diagram directed to a method of managing and determining the sobriety of a transportation driver using the biosensor device.

As shown in FIG. 9, a method of the present invention includes steps to identify and determine the sobriety of a transportation driver 13. For instance, at block 902, the method comprises the step of communicatively coupling a communication device (or the transportation-services device 2027) to a biosensor collector 32a. At block 905, the method includes the step of receiving a saliva or condensate sample from air exhaled by the transportation driver 13.

At block 910, the method includes the step of directing the saliva or condensate sample through a DNA sensor or directly through an intoxication sensor.

At block 920, the method is also comprised of the step of comparing cell material in the saliva or condensate sample to a DNA profile associated with the transportation driver to determine if said cell material matches the DNA profile of the transportation driver for verifying the identification of said driver, the DNA profile being stored in a database.

At block 925, the method advantageously includes the step of directing the saliva or condensate sample through an intoxication substance sensor if said cell material matches the DNA profile of the transportation driver At block 930, the method further includes the step of using an intoxication substance sensor to sense and determine the sobriety of the transportation driver to detect and measure the presence of alcohol and at least one intoxicating substance in the biological system of said driver within a preselected length of time with respect to a plurality of intoxicating substances from the cell material in the saliva or condensate sample taken from said driver.

Optionally, at block 940, the method comprises the step of allowing a transportation provider and consumer to monitor and determine the sobriety results of a driver.

Optionally, the community-based transportation services network 15 or the biosensor collector device 32 is configured to monitor and determine the sobriety of a transportation driver 13b. The network 15 and/or device(s) 32 advantageously include at least one community-based services processor 15p and/or at least one biosensor processor 32p suitably configured to perform a predefined set of basic operations in response to receiving a corresponding basic instruction selected from a predefined native instruction set of codes. The at least one community-based services processor 15p is communicatively coupled to a memory 15m and/or the at least one biosensor processor 32p is communicatively coupled to biosensor memory 32m. The memory 15m/32m comprises instructions that when executed by the processor(s) 15p/32p performs operations comprising at least one set of machine codes selected from the native instruction set for executing a sequence of operations/functions/steps stored in the memory 15m/32m. The resulting data from the executed functions/operations/steps are communicatively transmitted to the user's communication device 20 and/or to the transportation-provider network 28, and/or to the transportation-services device 2027, thereby enabling a first user or a transportation provider to monitor the sobriety of a transportation driver.

It should be understood that the foregoing relates to exemplary embodiments of the invention and that modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

INDUSTRIAL APPLICABILITY

The present invention pertains to a community-based transportation services system and method suitably configured to determine the location of parking-spots, register and offer parking-spots for rent or a fee, and monitor and determine the sobriety of a transportation driver which may be of value or importance to various industries such as, but not limited to, the travel and/or transportation industry, technology industry, or service and luxury industry.

What is claimed is:

1. A community-based transportation services system comprising:
 a transportation-services device communicatively coupled to a community-based transportation services network;
 the community-based transportation services network having a processor;
 a memory communicatively coupled to the processor, the memory comprising instructions that when executed by the processor performs operations comprising:
  determining, by receiving geographic data from the transportation-services device, a geographic earth location of a destination point of interest selected by a first user;
  monitoring an amount of traffic within a vicinity of the destination point of interest to determine when the destination point of interest is located in an area having saturated traffic;
  displaying a location of available parking-spots stored in the community-based transportation services network to the first user, the available parking-spots being located within a preselected radius of the geographic earth location of the destination point of Interest when the destination point of interest is determined to be located in the area having saturated traffic to help divert traffic therefrom;
  allowing the first user to select an available parking-spot stored in the community-based transportation services network, thereby enabling the first user to rent or pay a fee to park his or her vehicle in the available parking-spot;
  providing directions to the first user corresponding to the available parking-spot selected to allow the first user to park his or her vehicle;
  allowing the first user to contact a transportation driver to obtain a ride to the destination point of interest when the destination point of interest is determined to be located in the area having saturated traffic;
 a biosensor collector device communicatively coupled to the community-based transportation services network, wherein the memory further comprises instructions that when executed by the processor performs operations comprising:
  receiving sobriety-monitoring data associated with cell material disposed in a saliva or condensate sample from air exhaled by the transportation driver;
  allowing an intoxication substance sensor to receive the sobriety-monitoring data by directing the saliva or condensate sample through the intoxication substance sensor, the intoxication substance sensor being communicatively coupled to the biosensor collector device;
  analyzing the sobriety-monitoring data by using the intoxication substance sensor to sense and determine the sobriety of the transportation driver by detecting and measuring the presence of alcohol and at least one intoxicating substance in the biological system of said driver; and
  allowing the first user to observe the sobriety-data results, thereby enabling the first user to make an informed decision when deciding to use the services of a transportation provider.

2. The community-based transportation services system of claim 1, wherein the community-based transportation services network is comprised of a cloud server, a database and a primary communication device.

3. The community-based transportation services system of claim 1, wherein the memory further comprises instructions that when executed by the processor performs the operation comprising:
 allowing a second user to register at least one parking-spot with the community-based transportation services network utilizing the transportation-services device.

4. The community-based transportation services system of claim 3, wherein the geographic earth location of the at least one parking-spot registered to the community-based transportation services network is stored, entered or recorded into the database of the community-based transportation services network by:
 the second user providing an address of the at least one parking-spot; or
 a GNSS receiver configured to provide the geographic earth location of the at least one parking-spot to the community-based transportation services network or to the parking inventory database, wherein the GNSS receiver is a GPS, GLONASS, Galileo, IRNSS, QZSS, or Beidou satellite receiver; or
 the second user providing a name, address and picture of the parking facility corresponding to the at least one parking-spot.

5. The community-based transportation services system of claim of claim 1, wherein the memory further comprises instructions that when executed by the processor performs operations comprising:
 allowing the first user to reserve an available parking-spot utilizing the transportation-services device; and
 allowing the first user to request parking-spot availability updates utilizing the transportation-services device, wherein the requested parking-spot availability updates include the community-based transportation services network configured to communicate periodic updates to the transportation-services device.

6. The community-based transportation services system of claim of claim 1, wherein the transportation-services device displays an exact geographic earth location or address of the available parking-spot selected by the first user, and wherein the destination point of interest is a region of interest, an intersection, restaurant, theater, hotel, shopping centers, event, beach, retreat, golf course, pub, brewery, winery, casino, theme park, retreat, park, hiking or bicycle trail, ski resort, or tourist attraction.

7. The community-based transportation services system of claim of claim 1, wherein the transportation-services device is a mobile device, wherein said mobile device is a tablet computer, a smartphone, a personal computer, a server, or a handheld computer, wherein said mobile device is configured to have internet access for communicating with the community-based transportation services network, wherein said mobile device includes a software application program configured to manage and determine the location of said parking-spots, and wherein said mobile device further includes a Global Navigation Satellite System (GNSS) receiver utilized to determine the geographic earth location of the user or the destination point of interest selected by the user, wherein the GNSS receiver is a GPS, GLONASS, Galileo, IRNSS, QZSS, or Beidou satellite receiver.

8. The community-based transportation services system of claim 1, wherein the memory further comprises instructions that when executed by the processor performs operations comprising:
  directing the sobriety-monitoring data through a DNA sensor from air exhaled by a transportation driver prior to directing the saliva or condensate sample through the intoxication substance, the DNA sensor being communicatively coupled to the biosensor collector device;
  comparing the sobriety-monitoring data to a DNA profile data associated with the transportation driver to determine if said cell material matches the DNA profile of the transportation driver to verify the identification of said driver, the DNA profile data being stored in the community-based transportation services network; and
  allowing the intoxication substance sensor to receive the sobriety-monitoring data by directing the saliva or condensate sample through the intoxication substance sensor if said cell material in the saliva or condensate sample matches the DNA profile data of the transportation driver.

9. The community-based transportation services system of claim of claim 1, wherein the memory further comprises instructions that when executed by the processor performs operations comprising:
  using the intoxication substance sensor to analyze the sobriety-monitoring data by determining and measuring the intoxication level of said driver within a preselected length of time with respect to a plurality of intoxicating substances and alcohol; and
  providing the results of the analysis associated with the sobriety-monitoring data to a transportation-provider network and to the transportation-services device, thereby enabling the first user and a transportation provider to view and monitor the sobriety results of said driver.

10. A method of managing a community-based transportation services system, the method comprising the steps of:
  determining, by receiving geographic information from a transportation-services device, a geographic earth location of a destination point of Interest selected by a first user, the transportation-services device being communicatively coupled to a community-based transportation services network;
  monitoring an amount of traffic within a vicinity of the destination point of interest to determine when the destination point of interest is located in an area having saturated traffic;
  displaying a location of available parking-spots stored in the community-based transportation services network to the first user, the available parking-spots being located within a preselected radius of the geographic earth location of the destination point of interest when the destination point of interest is determined to be located in the area having saturated traffic to help divert traffic therefrom;
  allowing the first user to select an available parking-spot stored in the community-based transportation services network, thereby enabling the first user to rent or pay a fee to park his or her vehicle in the available parking-spot;
  providing directions to the first user corresponding to the available parking-spot selected by the first user, thereby allowing the first user to park his or her vehicle;
  allowing the first user to contact a transportation driver to obtain a ride to the destination point of interest;
  receiving sobriety-monitoring data associated with cell material disposed in a saliva or condensate sample from air exhaled by the transportation driver;
  allowing an intoxication substance sensor to receive the sobriety-monitoring data by directing the saliva or condensate sample through an intoxication substance sensor, the intoxication substance sensor being communicatively coupled to the biosensor collector device;
  analyzing the sobriety-monitoring data by using the intoxication substance sensor to sense and determine the sobriety of the transportation driver by detecting and measuring the presence of alcohol and at least one intoxicating substance in the biological system of said driver; and
  allowing the first user to observe the sobriety-data results, thereby enabling the first user to make an informed decision when deciding to use the services of a transportation provider.

11. The method of claim 10, wherein the community-based transportation services network is comprised of a cloud server, a database and a primary communication device.

12. The method of claim 10 further comprising the step of:
  allowing a second user to register at least one parking-spot with the community-based transportation services network using the transportation-services device to allow the first A user to rent or pay a fee to park his or her vehicle in the at least one parking-spot.

13. The method of claim 12, wherein the geographic earth location of the at least one parking-spot registered to the community-based transportation services network is stored, entered or recorded into the database of the community-based transportation services network by:
  the second user providing an address of the at least one parking-spot; or
  a GNSS receiver configured to provide the geographic earth location of the at least one parking-spot to the community-based transportation services network or to the parking inventory database, wherein the GNSS receiver is a GPS, GLONASS, Galileo, IRNSS, QZSS, or Beidou satellite receiver; or
  the second user providing a name, address and picture of the parking facility corresponding to the at least one parking-spot.

14. The method of claim 10 further comprising the steps of:
  allowing the first user to reserve an available parking-spot utilizing the transportation-services device; and
  allowing the first user to request parking-spot availability updates utilizing the transportation-services device, wherein the requested parking-spot availability updates include the community-based transportation services network configured to communicate periodic updates to the transportation-services device.

15. The method of claim 10, wherein the transportation-services device displays an exact geographic earth location or address of the available parking-spot selected by the first user, and wherein the destination point of interest is a region of interest, an intersection, restaurant, theater, hotel, shopping centers, event, beach, retreat, golf course, pub, brewery, winery, casino, theme park, retreat, park, hiking or bicycle trail, ski resort, or tourist attraction.

16. The method of claim 10, wherein the transportation-services device is a mobile device, wherein said mobile device is a tablet computer, a smartphone, a personal computer, a server, or a handheld computer, wherein said mobile device is configured to have internet access to communicate with the community-based transportation services network, wherein said mobile device includes a software application program configured to manage and determine the location of said parking-spots, and wherein said mobile device further includes a Global Navigation Satellite System (GNSS) receiver utilized to determine the geographic earth location of the user or the destination point of interest selected by the user, wherein the GNSS receiver is a GPS, GLONASS, Galileo, IRNSS, QZSS, or Beidou satellite receiver.

17. The method of claim 10 further comprising the steps of:
- directing the saliva or condensate sample through a DNA sensor, the DNA sensor being communicatively coupled to the biosensor collector device;
- comparing cell material disposed in the saliva or condensate sample to a DNA profile associated with the transportation driver to determine if said cell material matches the DNA profile of the transportation driver to verify the identification of said driver, the DNA profile being stored in the community-based transportation services network;
- directing the saliva or condensate sample through an intoxication substance sensor if said cell material matches the DNA profile of the transportation driver to sense and determine the sobriety of the transportation driver via the intoxication substance sensor.

18. The method of claim 17 further comprising the steps of:
- using the intoxication substance sensor to determine and measure the intoxication level of said driver within a preselected length of time with respect to a plurality of intoxicating substances and alcohol; and
- providing the data associated with the intoxication level of said driver to a transportation-provider network and to the transportation-services device, thereby enabling the first user and a transportation provider to view and monitor the sobriety results of said driver.

19. A system for monitoring the sobriety of a transportation driver, the system comprising:
- a biosensor collector device communicatively coupled to a community-based transportation services network, the community-based transportation services network having a processor;
- a memory communicatively coupled to the processor, the memory comprising instructions that when executed by the processor performs operations comprising:
  - allowing a first user to select a destination point of interest via a transportation-services device, wherein the transportation-services device is communicatively coupled to the community-based transportation services network;
  - monitoring an amount of traffic within a vicinity of the destination point of interest to determine when the destination point of interest is located in an area having saturated traffic;
  - allowing the first user to select an availability of parking-soot located within a pre-selected distance of the destination point of interest when the destination point of interest is determined to be located in the area having saturated traffic, thereby enabling the first user to park his or her vehicle away from the saturated traffic;
  - allowing the first user, via the transportation-services device, to contact a transportation provider to obtain a ride to the destination point of interest,
  - receiving sobriety-monitoring data associated with cell material disposed in a saliva or condensate sample associated with the transportation driver, wherein the transportation driver being associated with the transportation provider;
  - directing the saliva or condensate sample through a DNA sensor from air exhaled by a transportation driver, the DNA sensor being communicatively coupled to the biosensor collector device;
  - comparing the sobriety-monitoring data to a DNA profile data associated with the transportation driver to determine if said cell material matches the DNA profile of the transportation driver to verify the identification of said driver, the DNA profile data being stored in the community-based transportation services network;
  - allowing an intoxication substance sensor to receive the sobriety-monitoring data by directing the saliva or condensate sample through the intoxication substance sensor, the intoxication substance sensor being communicatively coupled to the biosensor collector device;
  - analyzing the sobriety-monitoring data by using the intoxication substance sensor to sense and determine the sobriety of the transportation driver by detecting and measuring the presence of alcohol and at least one intoxicating substance in the biological system of said driver, and
  - allowing the first user to observe the sobriety-data results to allow the first user to make an informed decision when deciding to use the services of the transportation provider.

20. The system of claim of claim 19, wherein the memory further comprises instructions that when executed by the processor performs operations comprising:
- using the intoxication substance sensor to analyze the sobriety-monitoring data by determining and measuring the intoxication level of said driver within a preselected length of time with respect to a plurality of intoxicating substances and alcohol; and
- providing the results of the analysis associated with the sobriety-monitoring data to a transportation-provider network and to the transportation-services device, thereby enabling a transportation provider to view and monitor the sobriety results of said driver.

* * * * *